United States Patent

Bergman et al.

(10) Patent No.: US 8,362,009 B2
(45) Date of Patent: Jan. 29, 2013

(54) SUBSTITUTED DIAZEPAN OREXIN RECEPTOR ANTAGONISTS

(75) Inventors: Jeffrey M. Bergman, Sellersville, PA (US); Paul J. Coleman, Wallingford, PA (US); Christopher D. Cox, Harleysville, PA (US); Anthony J. Roecker, North Wales, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 227 days.

(21) Appl. No.: 12/739,304

(22) PCT Filed: Oct. 27, 2008

(86) PCT No.: PCT/US2008/012182
§ 371 (c)(1),
(2), (4) Date: Apr. 22, 2010

(87) PCT Pub. No.: WO2009/058238
PCT Pub. Date: May 7, 2009

(65) Prior Publication Data
US 2010/0256121 A1    Oct. 7, 2010

Related U.S. Application Data

(60) Provisional application No. 61/000,760, filed on Oct. 29, 2007.

(51) Int. Cl.
*A61P 43/00* (2006.01)
*A61K 31/551* (2006.01)
*C07D 243/06* (2006.01)

(52) U.S. Cl. .......... 514/218; 540/575
(58) Field of Classification Search ........ 514/218; 540/575
See application file for complete search history.

(56) References Cited

U.S. PATENT DOCUMENTS

| 5,932,571 | A  | 8/1999  | Maynard et al. |
|---|---|---|---|
| 7,812,031 | B2 | 10/2010 | Aranyi et al. |
| 7,951,797 | B2 | 5/2011  | Breslin et al. |
| 2003/0225065 | A1 | 12/2003 | Jacobsen et al. |
| 2004/0019039 | A1 | 1/2004  | Dorwald et al. |
| 2007/0043037 | A1 | 2/2007  | Aranyi et al. |
| 2008/0132490 | A1 | 6/2008  | Bergman et al. |
| 2009/0124603 | A1 | 5/2009  | Brashear et al. |
| 2009/0192143 | A1 | 7/2009  | Cox et al. |
| 2009/0239843 | A1 | 9/2009  | Coleman et al. |

FOREIGN PATENT DOCUMENTS

| WO | WO2005075458 | 8/2005 |
|---|---|---|
| WO | WO2007126935 | 11/2007 |
| WO | WO2008008518 | 1/2008 |

OTHER PUBLICATIONS

Supplementary European Search Report for EP 08 84 5507, Jun. 30, 2011.

*Primary Examiner* — Brenda Coleman
(74) *Attorney, Agent, or Firm* — J. Eric Thies; Gerard M. Devlin

(57) ABSTRACT

The present invention is directed to diazepan compounds which are antagonists of orexin receptors, and which are useful in the treatment of neurological and psychiatric disorders and diseases in which orexin receptors are involved. The invention is also directed to pharmaceutical compositions comprising these compounds and the use of these compounds and compositions in the treatment of such diseases in which orexin receptors are involved.

10 Claims, No Drawings

SUBSTITUTED DIAZEPAN OREXIN RECEPTOR ANTAGONISTS

CROSS REFERENCE TO RELATED APPLICATIONS

This application is a U.S. National Phase application under 35 U.S.C. §371 of PCT Application No. PCT/US2008/012182, filed Oct. 27, 2008, which claims priority under 35 U.S.C. §119(e) from U.S. Ser. No. 61/000,760, filed Oct. 29, 2007.

BACKGROUND OF THE INVENTION

The orexins (hypocretins) comprise two neuropeptides produced in the hypothalamus: the orexin A (OX-A) (a 33 amino acid peptide) and the orexin B (OX-B) (a 28 amino acid peptide) (Sakurai T. et al., Cell, 1998, 92, 573-585). Orexins are found to stimulate food consumption in rats suggesting a physiological role for these peptides as mediators in the central feedback mechanism that regulates feeding behaviour (Sakurai T. et al., Cell, 1998, 92, 573-585). Orexins regulate states of sleep and wakefulness opening potentially novel therapeutic approaches for narcoleptic or insomniac patients (Chemelli R. M. et al., Cell, 1999, 98, 437-451). Orexins have also been indicated as playing a role in arousal, reward, learning and memory (Harris, et al., Trends Neurosci., 2006, 29 (10), 571-577). Two orexin receptors have been cloned and characterized in mammals. They belong to the super family of G-protein coupled receptors (Sakurai T. et al., Cell, 1998, 92, 573-585): the orexin-1 receptor (OX or OX1R) is selective for OX-A and the orexin-2 receptor (OX2 or OX2R) is capable to bind OX-A as well as OX-B. The physiological actions in which orexins are presumed to participate are thought to be expressed via one or both of OX 1 receptor and OX 2 receptor as the two subtypes of orexin receptors.

Orexin receptors are found in the mammalian brain and may have numerous implications in pathologies such as depression; anxiety; addictions; obsessive compulsive disorder; affective neurosis; depressive neurosis; anxiety neurosis; dysthymic disorder; behaviour disorder; mood disorder; sexual dysfunction; psychosexual dysfunction; sex disorder; schizophrenia; manic depression; delirium; dementia; severe mental retardation and dyskinesias such as Huntington's disease and Tourette syndrome; eating disorders such as anorexia, bulimia, cachexia, and obesity; addictive feeding behaviors; binge/purge feeding behaviors; cardiovascular diseases; diabetes; appetite/taste disorders; emesis, vomiting, nausea; asthma; cancer; Parkinson's disease; Cushing's syndrome/disease; basophile adenoma; prolactinoma; hyperprolactinemia; hypophysis tumour/adenoma; hypothalamic diseases; inflammatory bowel disease; gastric diskinesia; gastric ulcers; Froehlich's syndrome; adrenohypophysis disease; hypophysis disease; adrenohypophysis hypofunction; adrenohypophysis hyperfunction; hypothalamic hypogonadism; Kallman's syndrome (anosmia, hyposmia); functional or psychogenic amenorrhea; hypopituitarism; hypothalamic hypothyroidism; hypothalamic-adrenal dysfunction; idiopathic hyperprolactinemia; hypothalamic disorders of growth hormone deficiency; idiopathic growth deficiency; dwarfism; gigantism; acromegaly; disturbed biological and circadian rhythms; sleep disturbances associated with diseases such as neurological disorders, neuropathic pain and restless leg syndrome; heart and lung diseases, acute and congestive heart failure; hypotension; hypertension; urinary retention; osteoporosis; angina pectoris; myocardinal infarction; ischemic or haemorrhagic stroke; subarachnoid haemorrhage; ulcers; allergies; benign prostatic hypertrophy; chronic renal failure; renal disease; impaired glucose tolerance; migraine; hyperalgesia; pain; enhanced or exaggerated sensitivity to pain such as hyperalgesia, causalgia, and allodynia; acute pain; burn pain; atypical facial pain; neuropathic pain; back pain; complex regional pain syndrome I and II; arthritic pain; sports injury pain; pain related to infection e.g. HIV, post-chemotherapy pain; post-stroke pain; post-operative pain; neuralgia; emesis, nausea, vomiting; conditions associated with visceral pain such as irritable bowel syndrome, and angina; migraine; urinary bladder incontinence e.g. urge incontinence; tolerance to narcotics or withdrawal from narcotics; sleep disorders; sleep apnea; narcolepsy; insomnia; parasomnia; jet lag syndrome; memory disorders; and neurodegenerative disorders including nosological entities such as disinhibition-dementia-parkinsonism-amyotrophy complex; pallido-ponto-nigral degeneration; epilepsy; seizure disorders and other diseases related to general orexin system dysfunction.

SUMMARY OF THE INVENTION

The present invention is directed to diazepan compounds which are antagonists of orexin receptors, and which are useful in the treatment or prevention of neurological and psychiatric disorders and diseases in which orexin receptors are involved. The invention is also directed to pharmaceutical compositions comprising these compounds and the use of these compounds and compositions in the prevention or treatment of such diseases in which orexin receptors are involved.

DETAILED DESCRIPTION OF THE INVENTION

The present invention is directed to compounds of the formula I:

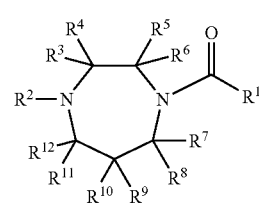

wherein:
$R^1$ is selected from the group consisting of:
  (1) phenyl, where the phenyl is substituted with $R^{1a}$, $R^{1b}$ and $R^{1c}$, and
  (2) napthyl, where the napthyl is substituted with $R^{1a}$, $R^{1b}$ and $R^{1c}$;
  (3) heteroaryl, where the heteroaryl is substituted with $R^{1a}$, $R^{1b}$ and $R^{1c}$;
$R^2$ is heteroaryl, where the heteroaryl is substituted with $R^{2a}$, $R^{2b}$ and $R^{2c}$;
$R^{1a}$, $R^{1b}$, $R^{1c}$, $R^{2a}$, $R^{2b}$ and $R^{2c}$ are independently selected from the group consisting of:
  (1) hydrogen,
  (2) halogen,
  (3) hydroxyl,
  (4) —(C=O)$_m$—O$_n$—C$_{1-6}$alkyl, where m is 0 or 1, n is 0 or 1 (wherein if m is 0 or n is 0, a bond is present) and where the alkyl is unsubstituted or substituted with one or more substituents selected from R$^{13}$, (5) —(C═O)$_m$—O$_n$—C$_{3-6}$cycloalkyl, where the cycloalkyl is unsubstituted or substituted with one or more substituents selected from R$^{13}$,
(6) —(C═O)$_m$—C$_{2-4}$alkenyl, where the alkenyl is unsubstituted or substituted with one or more substituents selected from R$^{13}$,
(7) —(C═O)$_m$—C$_{2-4}$alkynyl, where the alkynyl is unsubstituted or substituted with one or more substituents selected from R$^{13}$,
(8) —(C═O)$_m$—O$_n$-phenyl or —(C═O)$_m$—O$_n$-napthyl, where the phenyl or napthyl is unsubstituted or substituted with one or more substituents selected from R$^{13}$,
(9) —(C═O)$_m$—O$_n$-heterocycle, where the heterocycle is unsubstituted or substituted with one or more substituents selected from R$^{13}$,
(10) —(C═O)$_m$—NR$^{10}$R$^{11}$, wherein R$^{10}$ and R$^{11}$ are independently selected from the group consisting of:
  (a) hydrogen,
  (b) C$_{1-6}$alkyl, which is unsubstituted or substituted with one or more substituents selected from R$^{13}$,
  (c) C$_{3-6}$alkenyl, which is unsubstituted or substituted with one or more substituents selected from R$^{13}$,
  (d) cycloalkyl, which is unsubstituted or substituted with one or more substituents selected from R$^{13}$,
  (e) phenyl, which is unsubstituted or substituted with one or more substituents selected from R$^{13}$, and
  (f) heterocycle, which is unsubstituted or substituted with one or more substituents selected from R$^{13}$,
(11) —S(O)$_2$—NR$^{10}$R$^{11}$,
(12) —S(O)$_q$—R$^{12}$, where q is 0, 1 or 2 and where R$^{12}$ is selected from the definitions of R$^{10}$ and R$^{11}$,
(13) —CO$_2$H,
(14) —CN,
(15) —NO$_2$, and
(16) —B(OH)$_2$;
R$^3$, R$^4$, R$^5$, R$^6$, R$^7$, R$^8$, R$^9$, R$^{10}$, R$^{11}$ and R$^{12}$ are independently selected from the group consisting of:
(1) hydrogen,
(2) —C$_{1-6}$alkyl, where the alkyl is unsubstituted or substituted with one or more substituents selected from R$^{13}$,
(3) —O—C$_{1-6}$alkyl, where the alkyl is unsubstituted or substituted with one or more substituents selected from R$^{13}$, and
(4) -phenyl, where the phenyl is unsubstituted or substituted with one or more substituents selected from R$^{13}$,
or R$^3$ and R$^4$, or R$^5$ and R$^6$, or R$^7$ and R$^8$, or R$^9$ and R$^{10}$, or R$^{11}$ and R$^{12}$ are taken together to form a C$_{3-6}$cycloalkyl, where the cycloalkyl is unsubstituted or substituted with one or more substituents selected from R$^{14}$,
with the proviso that at least two of R$^3$, R$^4$, R$^5$, R$^6$, R$^7$, R$^8$, R$^9$, R$^{10}$, R$^{11}$ or R$^{12}$ are other than hydrogen;
R$^{13}$ is selected from the group consisting of:
(1) halogen,
(2) hydroxyl,
(3) —(C═O)$_m$—O$_n$—C$_{1-6}$alkyl, where the alkyl is unsubstituted or substituted with one or more substituents selected from R$^{14}$,
(4) —O$_n$—(C$_{1-3}$)perfluoroalkyl,
(5) —(C═O)$_m$—O$_n$—C$_{3-6}$cycloalkyl, where the cycloalkyl is unsubstituted or substituted with one or more substituents selected from R$^{14}$,
(6) —(C═O)$_m$—C$_{2-4}$alkenyl, where the alkenyl is unsubstituted or substituted with one or more substituents selected from R$^{14}$,
(7) —(C═O)$_m$—O$_n$-phenyl or —(C═O)$_m$—O$_n$-napthyl, where the phenyl or napthyl is unsubstituted or substituted with one or more substituents selected from R$^{14}$,
(8) —(C═O)$_m$—O$_n$-heterocycle, where the heterocycle is unsubstituted or substituted with one or more substituents selected from R$^{14}$,
(9) —(C═O)$_m$—NR$^{10}$R$^{11}$,
(10) —S(O)$_2$—NR$^{10}$R$^{11}$,
(11) —S(O)$_q$—R$^{12}$,
(12) —CO$_2$H,
(13) —CN, and
(14) —NO$_2$;
R$^{14}$ is selected from the group consisting of:
(1) hydroxyl,
(2) halogen,
(3) C$_{1-6}$alkyl,
(4) —C$_{3-6}$cycloalkyl,
(5) —O—C$_{1-6}$alkyl,
(6) —O(C═O)—C$_{1-6}$alkyl,
(7) —NH—C$_{1-6}$alkyl,
(8) phenyl,
(9) heterocycle,
(10) —CO$_2$H, and
(11) —CN;
or a pharmaceutically acceptable salt thereof.

An embodiment of the present invention includes compounds of the formula Ia:

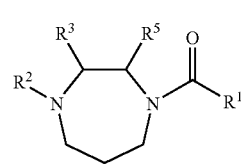

Ia wherein R$^1$, R$^2$, R$^3$ and R$^5$ are defined herein; or a pharmaceutically acceptable salt thereof.

An embodiment of the present invention includes compounds of the formula Ib:

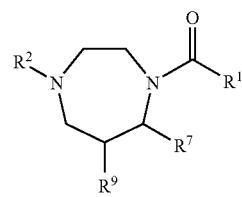

Ib wherein R$^1$, R$^2$, R$^7$ and R$^9$ are defined herein; or a pharmaceutically acceptable salt thereof.

An embodiment of the present invention includes compounds of the formula Ic:

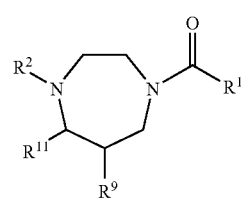

Ic wherein R$^1$, R$^2$, R$^9$ and R$^{11}$ are defined herein; or a pharmaceutically acceptable salt thereof.

An embodiment of the present invention includes compounds of the formula Id:

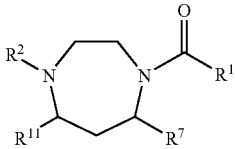

Id wherein $R^1$, $R^2$, $R^7$ and $R^{11}$ are defined herein; or a pharmaceutically acceptable salt thereof.

An embodiment of the present invention includes compounds of the formula Ie:

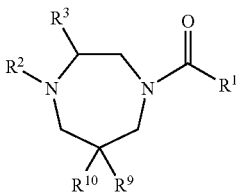

Ie wherein $R^1$, $R^2$, $R^3$, $R^9$ and $R^{10}$ are defined herein; or a pharmaceutically acceptable salt thereof.

An embodiment of the present invention includes compounds of the formula Ie':

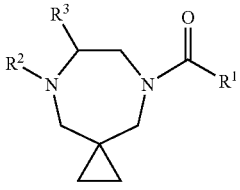

Ie' wherein $R^1$, $R^2$ and $R^3$ are defined herein; or a pharmaceutically acceptable salt thereof.

An embodiment of the present invention includes compounds of the formula If:

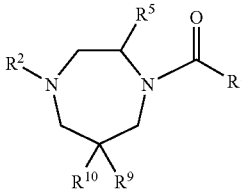

If wherein $R^1$, $R^2$, $R^5$, $R^9$ and $R^{10}$ are defined herein; or a pharmaceutically acceptable salt thereof.

An embodiment of the present invention includes compounds of the formula If':

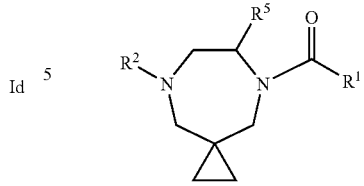

If' wherein $R^1$, $R^2$ and $R^5$ are defined herein; or a pharmaceutically acceptable salt thereof.

An embodiment of the present invention includes compounds wherein $R^1$ is phenyl, which is unsubstituted or substituted with one or more of:
(1) halogen,
(2) hydroxyl,
(3) —$O_n$—$C_{1-6}$alkyl, where n is 0 or 1 (wherein if n is 0, a bond is present) and where the alkyl is unsubstituted or substituted with one or more substituents selected from $R^{13}$,
(4) —$O_n$-phenyl, where the phenyl is unsubstituted or substituted with one or more substituents selected from $R^{13}$,
(5) -heterocycle, where the heterocycle is unsubstituted or substituted with one or more substituents selected from $R^{13}$,
(6) —$NR^{10}R^{11}$, wherein $R^{10}$ and $R^{11}$ are independently selected from the group consisting of:
  (a) hydrogen,
  (b) $C_{1-6}$alkyl, which is unsubstituted or substituted with one or more substituents selected from $R^{13}$,
(7) —$S(O)_2$—$NR^{10}R^{11}$,
(8) —$CO_2H$,
(9) —CN,
(10) —$NO_2$, and
(11) —$B(OH)_2$.

An embodiment of the present invention includes compounds wherein $R^1$ is phenyl, which is unsubstituted or substituted with one or more methyl, —$CF_3$, halo, —$OCF_3$, —$OCH_3$, —$OCH_2CH_3$, —$CO_2CH_3$, —CN, —$N(CH_3)$, —$NH(CH_2CH_3)$, —$NO_2$, —$B(OH)_2$, triazoly, thiazolyl or phenyl.

An embodiment of the present invention includes compounds wherein $R^1$ is phenyl, which is unsubstituted or substituted with one or more methyl, —$CF_3$, chloro, fluoro, —$OCF_3$, —$OCH_3$, —$OCH_2CH_3$, —$CO_2CH_3$, —$B(OH)_2$, triazolyl, thiazolyl or phenyl.

An embodiment of the present invention includes compounds wherein $R^1$ is phenyl, which is unsubstituted or substituted with one or more methyl, —$CF_3$, fluoro, —$OCF_3$, —$OCH_3$, —$CO_2CH_3$, —$B(OH)_2$, triazolyl, thiazolyl or phenyl.

An embodiment of the present invention includes compounds wherein $R^1$ is selected from the group consisting of:
(1) phenyl,
(2) biphenyl,
(3) 2,6-dimethoxyphenyl,
(4) 2,4-dichlorophenyl,
(5) 2,6-dichlorophenyl,
(6) 2,3-difluophenyl,
(7) 2,4-difluophenyl,
(8) 2,6-difluophenyl,
(9) 2-methoxy-4-methyl-phenyl,
(10) 3-methoxy-biphenyl,
(11) 3-methyl-biphenyl,
(12) 5-methyl-2-thiazolyl-phenyl, and
(13) 5-methyl-2-triazolyl-phenyl.

An embodiment of the present invention includes compounds wherein $R^1$ is phenyl. An embodiment of the present invention includes compounds wherein $R^1$ is 2,6-dimethoxyphenyl. An embodiment of the present invention includes compounds wherein $R^1$ is 5-methyl-2-thiazolyl-phenyl. An embodiment of the present invention includes compounds wherein $R^1$ is 5-methyl-2-triazolyl-phenyl.

An embodiment of the present invention includes compounds wherein $R^2$ is heteroaryl, which is unsubstituted or substituted with one or more of:
(1) halogen,
(2) hydroxyl,
(3) —$O_n$—$C_{1-6}$alkyl, where n is 0 or 1 (wherein if n is 0, a bond is present) and where the alkyl is unsubstituted or substituted with one or more substituents selected from $R^{13}$,
(4) —$O_n$-phenyl, where the phenyl is unsubstituted or substituted with one or more substituents selected from $R^{13}$,
(5) -heterocycle, where the heterocycle is unsubstituted or substituted with one or more substituents selected from $R^{13}$,
(6) —$NR^{10}R^{11}$, wherein $R^{10}$ and $R^{11}$ are independently selected from the group consisting of:
  (a) hydrogen,
  (b) $C_{1-6}$alkyl, which is unsubstituted or substituted with one or more substituents selected from $R^{13}$,
(7) —$S(O)_2$—$NR^{10}R^{11}$,
(8) —$CO_2H$,
(9) —CN, and
(10) —$NO_2$.

An embodiment of the present invention includes compounds wherein $R^2$ is heteroaryl, which is unsubstituted or substituted with halogen, hydroxyl, $C_{1-6}$ alkyl, —O—$C_{1-6}$alkyl or phenyl.

An embodiment of the present invention includes compounds wherein $R^2$ is selected from the group consisting of:
(1) benzimidazolyl,
(2) benzothiazolyl,
(3) benzoxazolyl,
(4) quinazolinyl,
(5) quinolinyl,
(6) thiadiazolyl,
(7) thiazolyl, and
(8) oxazolopyridyl,
which is unsubstituted or substituted with halogen, hydroxyl, $C_{1-6}$alkyl, —O—$C_{1-6}$alkyl or phenyl.

An embodiment of the present invention includes compounds wherein $R^2$ is selected from the group consisting of:
(1) benzimidazol-2-yl,
(2) 1,3-benzothiazol-2-yl,
(3) 1,3-benzoxazol-2-yl,
(4) 2-quinazolinyl,
(5) 1-quinolin-2-yl,
(6) 1,2,4-thiadiazol-5-yl,
(7) 1,3-thiazol-2-yl, and
(8) oxazolo[5,4-b]pyridyl,
which is unsubstituted or substituted with methyl, fluoro, chloro or phenyl.

An embodiment of the present invention includes compounds wherein $R^2$ is benzothiazolyl, which is unsubstituted or substituted with chloro. An embodiment of the present invention includes compounds wherein $R^2$ is 6-chloro-benzothiazolyl. An embodiment of the present invention includes compounds wherein $R^2$ is benzoxazolyl. An embodiment of the present invention includes compounds wherein $R^2$ is quinazolinyl or quinolinyl. An embodiment of the present invention includes compounds wherein $R^2$ is 6-fluoroquinazolinyl.

An embodiment of the present invention includes compounds wherein $R^3$, $R^4$, $R^5$, $R^6$, $R^7$, $R^8$, $R^9$, $R^{10}$, $R^{11}$ and $R^{12}$ are independently selected from the group consisting of:
(1) hydrogen,
(2) —$C_{1-6}$alkyl, where the alkyl is unsubstituted or substituted with one or more substituents selected from $R^{13}$,
or $R^3$ and $R^4$, or $R^5$ and $R^6$, or $R^7$ and $R^8$, or $R^9$ and $R^{10}$, or $R^{11}$ and $R^{12}$ are taken together to form a $C_{3-6}$cycloalkyl, where the cycloalkyl is unsubstituted or substituted with one or more substituents selected from $R^{14}$,
with the proviso that at least two of $R^3$, $R^4$, $R^5$, $R^6$, $R^7$, $R^8$, $R^9$, $R^{10}$, $R^{11}$ or $R^{12}$ are other than hydrogen.

An embodiment of the present invention includes compounds wherein $R^3$, $R^4$, $R^5$, $R^6$, $R^7$, $R^8$, $R^9$, $R^{10}$, $R^{11}$ and $R^{12}$ are independently selected from the group consisting of:
(1) hydrogen,
(2) —$C_{1-6}$alkyl,
or $R^3$ and $R^4$, or $R^5$ and $R^6$, or $R^7$ and $R^8$, or $R^9$ and $R^{10}$, or $R^{11}$ and $R^{12}$ are taken together to form a $C_{3-6}$cycloalkyl,
with the proviso that at least two of $R^3$, $R^4$, $R^5$, $R^6$, $R^7$, $R^8$, $R^9$, $R^{10}$, $R^{11}$ or $R^{12}$ are other than hydrogen.

An embodiment of the present invention includes compounds wherein $R^3$ is —$C_{1-6}$alkyl, $R^4$ is hydrogen, $R^5$ is —$C_{1-6}$alkyl, $R^6$ is hydrogen, $R^7$ is hydrogen, $R^8$ is hydrogen, $R^9$ is hydrogen, $R^{10}$ is hydrogen, $R^{11}$ is hydrogen and $R^{12}$ is hydrogen. Within this embodiment the present invention includes compounds wherein $R^3$ is methyl, $R^4$ is hydrogen, $R^5$ is methyl, $R^6$ is hydrogen, $R^7$ is hydrogen, $R^8$ is hydrogen, $R^9$ is hydrogen, $R^{10}$ is hydrogen, $R^{11}$ is hydrogen and $R^{12}$ is hydrogen.

An embodiment of the present invention includes compounds wherein $R^3$ is hydrogen, $R^4$ is hydrogen, $R^5$ is hydrogen, $R^6$ is hydrogen, $R^7$ is —$C_{1-6}$alkyl, $R^8$ is hydrogen, $R^9$ is —$C_{1-6}$alkyl, $R^{10}$ is hydrogen, $R^{11}$ is hydrogen and $R^{12}$ is hydrogen. Within this embodiment the present invention includes compounds wherein $R^3$ is hydrogen, $R^4$ is hydrogen, $R^5$ is hydrogen, $R^6$ is hydrogen, $R^7$ is methyl, $R^8$ is hydrogen, $R^9$ is methyl, $R^{10}$ is hydrogen, $R^{11}$ is hydrogen and $R^{12}$ is hydrogen.

An embodiment of the present invention includes compounds wherein $R^3$ is hydrogen, $R^4$ is hydrogen, $R^5$ is hydrogen, $R^6$ is hydrogen, $R^7$ is hydrogen, $R^8$ is hydrogen, $R^9$ is —$C_{1-6}$alkyl, $R^{10}$ is hydrogen, $R^{11}$ is $C_{1-6}$alkyl, and $R^{12}$ is hydrogen. Within this embodiment the present invention includes compounds wherein $R^3$ is hydrogen, $R^4$ is hydrogen, $R^5$ is hydrogen, $R^6$ is hydrogen, $R^7$ is hydrogen, $R^8$ is hydrogen, $R^9$ is methyl, $R^{10}$ is hydrogen, $R^{11}$ is methyl and $R^{12}$ is hydrogen.

An embodiment of the present invention includes compounds wherein $R^3$ is hydrogen, $R^4$ is hydrogen, $R^5$ is hydrogen, $R^6$ is hydrogen, $R^7$ is —$C_{1-6}$alkyl, $R^8$ is hydrogen, $R^9$ is hydrogen, $R^{10}$ is hydrogen, $R^{11}$ is —$C_{1-6}$ alkyl and $R^{12}$ is hydrogen. Within this embodiment the present invention includes compounds wherein $R^3$ is hydrogen, $R^4$ is hydrogen, $R^5$ is hydrogen, $R^6$ is hydrogen, $R^7$ is -methyl, $R^8$ is hydrogen, $R^9$ is hydrogen, $R^{10}$ is hydrogen, $R^{11}$ is methyl and $R^{12}$ is hydrogen.

An embodiment of the present invention includes compounds wherein $R^3$ is —$C_{1-6}$alkyl, $R^4$ is hydrogen, $R^5$ is hydrogen, $R^6$ is hydrogen, $R^7$ is hydrogen, $R^8$ is hydrogen, $R^9$ and $R^{10}$ taken together are $C_{3-6}$cycloalkyl, $R^{11}$ is hydrogen and $R^{12}$ is hydrogen. Within this embodiment the present invention includes compounds wherein $R^3$ is methyl, $R^4$ is hydrogen, $R^5$ is hydrogen, $R^6$ is hydrogen, $R^7$ is hydrogen, $R^8$ is hydrogen, $R^9$ and $R^{10}$ taken together are cyclopropyl, $R^{11}$ is hydrogen and $R^{12}$ is hydrogen.

An embodiment of the present invention includes compounds wherein $R^3$ is hydrogen, $R^4$ is hydrogen, $R^5$ is —$C_{1-6}$alkyl, $R^6$ is hydrogen, $R^7$ is hydrogen, $R^8$ is hydrogen, $R^9$ and $R^{10}$ taken together are $C_{3-6}$cycloalkyl, $R^{11}$ is hydrogen and $R^{12}$ is hydrogen. Within this embodiment the present invention includes compounds wherein $R^3$ is hydrogen, $R^4$ is hydrogen, $R^5$ is methyl, $R^6$ is hydrogen, $R^7$ is hydrogen, $R^8$ is hydrogen, $R^9$ and $R^{10}$ taken together are cyclopropyl, $R^{11}$ is hydrogen and $R^{12}$ is hydrogen.

Specific embodiments of the present invention include a compound which is selected from the group consisting of the subject compounds of the Examples herein or a pharmaceutically acceptable salt thereof.

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The present invention is meant to comprehend all such isomeric forms of these compounds. Formula I shows the structure of the class of compounds without specific stereochemistry.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art. Alternatively, any enantiomer of a compound may be obtained by stereoselective synthesis using optically pure starting materials or reagents of known configuration by methods well known in the art.

As appreciated by those of skill in the art, halogen or halo as used herein are intended to include fluoro, chloro, bromo and iodo. Similarly, $C_{1-6}$, as in $C_{1-6}$alkyl is defined to identify the group as having 1, 2, 3, 4, 5 or 6 carbons in a linear or branched arrangement, such that $C_{1-8}$alkyl specifically includes methyl, ethyl, n-propyl, iso-propyl, n-butyl, iso-butyl, tert-butyl, pentyl, and hexyl. A group which is designated as being independently substituted with substituents may be independently substituted with multiple numbers of such substituents. The term "heterocycle" as used herein includes both unsaturated and saturated heterocyclic moieties, wherein the unsaturated heterocyclic moieties (i.e. "heteroaryl") include benzoimidazolyl, benzimidazolonyl, benzofuranyl, benzofurazanyl, benzopyrazolyl, benzothiazolyl, benzotriazolyl, benzothiophenyl, benzoxazepin, benzoxazolyl, carbazolyl, carbolinyl, cinnolinyl, furanyl, imidazolyl, indolinyl, indolyl, dihydroindolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydroquinoxalinyl, tetrazolyl, tetrazolopyridyl, thiadiazolyl, thiazolyl, thienyl, triazolyl, and N-oxides thereof, and wherein the saturated heterocyclic moieties include azetidinyl, 1,4-dioxanyl, hexahydroazepinyl, piperazinyl, piperidinyl, pyridin-2-onyl, pyrrolidinyl, morpholinyl, tetrahydrofuranyl, thiomorpholinyl, and tetrahydrothienyl, and N-oxides thereof.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particular embodiments include the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particular embodiments include the citric, hydrobromic, hydrochloric, maleic, phosphoric, sulfuric, fumaric, and tartaric acids. It will be understood that, as used herein, references to the compounds of Formula I are meant to also include the pharmaceutically acceptable salts.

Exemplifying the invention is the use of the compounds disclosed in the Examples and herein. Specific compounds within the present invention include a compound which selected from the group consisting of the compounds disclosed in the following Examples and pharmaceutically acceptable salts thereof and individual enantiomers or diastereomers thereof.

The subject compounds are useful in a method of antagonizing orexin receptor activity in a patient such as a mammal in need of such inhibition comprising the administration of an effective amount of the compound. The present invention is directed to the use of the compounds disclosed herein as antagonists of orexin receptor activity. In addition to primates, especially humans, a variety of other mammals can be treated according to the method of the present invention. The present invention is directed to a compound of the present invention or a pharmaceutically acceptable salt thereof for use in medicine. The present invention is further directed to a use of a compound of the present invention or a pharmaceutically acceptable salt thereof for the manufacture of a medicament for antagonizing orexin receptor activity or treating the disorders and diseases noted herein in humans and animals.

The subject treated in the present methods is generally a mammal, such as a human being, male or female. The term "therapeutically effective amount" means the amount of the subject compound that will elicit the biological or medical response of a tissue, system, animal or human that is being sought by the researcher, veterinarian, medical doctor or other clinician. It is recognized that one skilled in the art may affect the neurological and psychiatric disorders by treating a patient presently afflicted with the disorders or by prophylactically treating a patient afflicted with the disorders with an effective amount of the compound of the present invention. As used herein, the terms "treatment" and "treating" refer to all processes wherein there may be a slowing, interrupting, arresting, controlling, or stopping of the progression of the neurological and psychiatric disorders described herein, but does not necessarily indicate a total elimination of all disorder symptoms, as well as the prophylactic therapy of the mentioned conditions, particularly in a patient who is predisposed to such disease or disorder. The terms "administration of" and or "administering a" compound should be understood to mean providing a compound of the invention or a prodrug of a compound of the invention to the individual in need thereof.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The utility of the compounds in accordance with the present invention as orexin receptor OX1R and/or OX2R antagonists may be readily determined without undue experimentation by methodology well known in the art, including the "FLIPR $Ca^{2+}$ Flux Assay" (Okumura et al., Biochem. Biophys. Res. Comm. 280:976-981, 2001). In a typical experiment the OX1 and OX2 receptor antagonistic activity of the compounds of the present invention was determined in accordance with the following experimental method. For intracellular calcium measurements, Chinese hamster ovary (CHO) cells expressing the rat orexin-1 receptor or the human orexin-2 receptor, are grown in Iscove's modified DMEM containing 2 mM L-glutamine, 0.5 g/ml G418, 1% hypoxanthine-thymidine supplement, 100 U/ml penicillin, 100 ug/ml streptomycin and 10% heat-inactivated fetal calf serum (FCS). The cells are seeded at 20,000 cells/well into Becton-Dickinson black 384-well clear bottom sterile plates coated with poly-D-lysine. All reagents were from GIBCO-Invitrogen Corp. The seeded plates are incubated overnight at 37° C. and 5% CO2. Ala-6,12 human orexin-A as the agonist is prepared as a 1 mM stock solution in 1% bovine serum albumin (BSA) and diluted in assay buffer (HBSS containing 20 mM HEPES, 0.1% BSA and 2.5 mM probenecid, pH7.4) for use in the assay at a final concentration of 70 pM. Test compounds are prepared as 10 mM stock solution in DMSO, then diluted in 384-well plates, first in DMSO, then assay buffer. On the day of the assay, cells are washed 3 times with 100 ul assay buffer and then incubated for 60 min (37° C., 5% CO2) in 60 ul assay buffer containing 1 uM Fluo-4AM ester, 0.02% pluronic acid, and 1% BSA. The dye loading solution is then aspirated and cells are washed 3 times with 100 ul assay buffer. 30 ul of that same buffer is left in each well. Within the Fluorescent Imaging Plate Reader (FLIPR, Molecular Devices), test compounds are added to the plate in a volume of 25 ul, incubated for 5 min and finally 25 ul of agonist is added. Fluorescence is measured for each well at 1 second intervals for 5 minutes and the height of each fluorescence peak is compared to the height of the fluorescence peak induced by 70 pM Ala-6,12 orexin-A with buffer in place of antagonist. For each antagonist, IC50 value (the concentration of compound needed to inhibit 50% of the agonist response) is determined. The intrinsic orexin receptor antagonist activity of a compound which may be used in the present invention may be determined by these assays.

In particular, the compounds of the following examples had activity in antagonizing the rat orexin-1 receptor and/or the human orexin-2 receptor in the aforementioned assays, generally with an $IC_{50}$ of less than about 50 μM. Many of compounds within the present invention had activity in antagonizing the rat orexin-1 receptor and/or the human orexin-2 receptor in the aforementioned assays with an $IC_{50}$ of less than about 100 nM. Such a result is indicative of the intrinsic activity of the compounds in use as antagonists of orexin-1 receptor and/or the orexin-2 receptor. The present invention also includes compounds within the generic scope of the invention which possess activity as agonists of the orexin-1 receptor and/or the orexin-2 receptor. With respect to other diazepan compounds, the present compounds exhibit unexpected properties, such as with respect to increased oral bioavailability, metabolic stability, decreased inhibition of metabolic enzymes (such as decreased cytochrome P450 3A4 (CYP3A4) inhibition), decreased inhibition of transporters (such as decreased p-glycoprotein/PGP inhibition) and/or selectivity with respect to other receptors, including the human orexin-2 receptor.

The orexin receptors have been implicated in a wide range of biological functions. This has suggested a potential role for these receptors in a variety of disease processes in humans or other species. The compounds of the present invention have utility in treating, preventing, ameliorating, controlling or reducing the risk of a variety of neurological or psychiatric disorders associated with orexin receptors or in which orexin receptors are involved. The compounds of the present invention have utility in treating, preventing, ameliorating, controlling or reducing the risk of one or more of the following conditions or diseases: sleep disorders, sleep disturbances, including enhancing sleep quality, improving sleep quality, increasing sleep efficiency, augmenting sleep maintenance; increasing the value which is calculated from the time that a subject sleeps divided by the time that a subject is attempting to sleep; improving sleep initiation; decreasing sleep latency or onset (the time it takes to fall asleep); decreasing difficulties in falling asleep; increasing, sleep continuity; decreasing the number of awakenings during sleep; decreasing intermittent wakings during sleep; decreasing nocturnal arousals; decreasing the time spent awake following the initial onset of sleep; increasing the total amount of sleep; reducing the fragmentation of sleep; altering the timing, frequency or duration of REM sleep bouts; altering the timing, frequency or duration of slow wave (i.e. stages 3 or 4) sleep bouts; increasing the amount and percentage of stage 2 sleep; promoting slow wave sleep; enhancing EEG-delta activity during sleep; decreasing nocturnal arousals, especially early morning awakenings; increasing daytime alertness; reducing daytime drowsiness; treating or reducing excessive daytime sleepiness; increasing satisfaction with the intensity of sleep; increasing sleep maintenance; idiopathic insomnia; sleep problems; insomnia, hypersomnia, idiopathic hypersomnia, repeatability hypersomnia, intrinsic hypersomnia, narcolepsy, interrupted sleep, sleep apnea, wakefulness, nocturnal myoclonus, REM sleep interruptions, jet-lag, shift workers' sleep disturbances, dyssomnias, night terror, insomnias associated with depression, emotional/mood disorders, Alzheimer's disease or cognitive impairment, as well as sleep walking and enuresis, and sleep disorders which accompany aging; Alzheimer's sundowning; conditions associated with circadian rhythmicity as well as mental and physical disorders associated with travel across time zones and with rotating shift-work schedules, conditions due to drugs which cause reductions in REM sleep as a side effect; fibromyalgia; syndromes which are manifested by non-restorative sleep and muscle pain or sleep apnea which is associated with respiratory disturbances during sleep; conditions which result from a diminished quality of sleep; increasing learning, augmenting memory, increasing memory function and performance, increasing retention of memory, enhancing memory, maintaining memory, restoring memory, including all stages and/or types of short-term, middle-term and long-term memory; eating disorders associated with excessive food intake and complications associated therewith, compulsive eating disorders, obesity (due to any cause, whether genetic or environmental), obesity-related disorders including overeating and bulimia nervosa, hypertension, diabetes, elevated plasma insulin concentrations and insulin resistance, dyslipidemias, hyperlipidemia, endometrial, breast, prostate and colon cancer, osteoarthritis, obstructive sleep apnea, cholelithiasis, gallstones, heart disease, abnormal heart rhythms and arrythmias, myocardial infarction, congestive heart failure, coronary heart disease, sudden death, stroke, polycystic ovary disease, craniopharyngioma, the Prader-Willi Syndrome, Frohlich's syndrome, GH-deficient subjects, normal variant short stature, Turner's syndrome, and other pathological conditions showing reduced metabolic activity or a decrease in resting energy expenditure as a percentage of total fat-free mass, e.g, children with acute lymphoblastic leukemia, metabolic syndrome, also known as syndrome X, insulin resistance syndrome, reproductive hormone abnormalities, sexual and reproductive dysfunction, such as impaired fertility, infertility, hypogonadism in males and hirsutism in females, fetal defects associated with maternal obesity, gastrointestinal motility disorders, such as obesity-related gastro-esophageal reflux, respiratory disorders, such as obesity-hypoventilation syndrome (Pickwickian syndrome), breathlessness, cardiovascular disorders, inflammation, such as systemic inflammation of the vasculature, arteriosclerosis, hypercholesterolemia, hyperuricaemia, lower back pain, gallbladder disease, gout, kidney cancer, increased anesthetic risk, reducing the risk of secondary outcomes of obesity, such as reducing the risk of left ventricular hypertrophy; diseases or disorders where abnormal oscillatory activity occurs in the brain, including depression, migraine, neuropathic pain, Parkinson's disease, psychosis and schizophrenia, as well as diseases or disorders where there is abnormal coupling of activity, particularly through the thalamus; enhancing cognitive function; enhancing memory; increasing memory retention; increasing immune response; increasing immune function; hot flashes; night sweats; extending life span; schizophrenia; muscle-related disorders that are controlled by the excitation/relaxation rhythms imposed by the neural system such as cardiac rhythm and other disorders of the cardiovascular system; conditions related to proliferation of cells such as vasodilation or vasorestriction and blood pressure; cancer; cardiac arrhythmia; hypertension; congestive heart failure; conditions of the genital/urinary system; disorders of sexual function and fertility; adequacy of renal function; responsivity to anesthetics; mood disorders, such as depression or more particularly depressive disorders, for example, single episodic or recurrent major depressive disorders and dysthymic disorders, or bipolar disorders, for example, bipolar I disorder, bipolar II disorder and cyclothymic disorder, mood disorders due to a general medical condition, and substance-induced mood disorders, atypical depression; anxiety disorders including acute stress disorder, agoraphobia, generalized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition; acute neurological and psychiatric disorders such as cerebral deficits subsequent to cardiac bypass surgery and grafting, stroke, ischemic stroke, cerebral ischemia, spinal cord trauma, head trauma, perinatal hypoxia, cardiac arrest, hypoglycemic neuronal damage; Huntington's Chorea; amyotrophic lateral sclerosis; multiple sclerosis; ocular damage; retinopathy; cognitive disorders; idiopathic and drug-induced Parkinson's disease; muscular spasms and disorders associated with muscular spasticity including tremors, epilepsy, convulsions; cognitive disorders including dementia (associated with Alzheimer's disease, ischemia, trauma, vascular problems or stroke, HIV disease, Parkinson's disease, Huntington's disease, Pick's disease, Creutzfeldt-Jacob disease, perinatal hypoxia, other general medical conditions or substance abuse); delirium, amnestic disorders or age related cognitive decline; schizophrenia or psychosis including schizophrenia (paranoid, disorganized, catatonic or undifferentiated), schizophreniform disorder, schizoaffective disorder, delusional disorder, brief psychotic disorder, shared psychotic disorder, psychotic disorder due to a general medical condition and substance-induced psychotic disorder; substance-related disorders, substance abuse, addiction and addictive behaviors, reward-related behaviors (including substance-induced delirium, persisting dementia, persisting amnestic disorder, psychotic disorder or anxiety disorder; tolerance, addictive feeding, dependence, withdrawal or relapse from substances including alcohol, amphetamines, cannabis, cocaine, hallucinogens, inhalants, nicotine, opioids, phencyclidine, sedatives, hypnotics or anxiolytics); movement disorders, including akinesias and akinetic-rigid syndromes (including Parkinson's disease, drug-induced parkinsonism, postencephalitic parkinsonism, progressive supranuclear palsy, multiple system atrophy, corticobasal degeneration, parkinsonism-ALS dementia complex and basal ganglia calcification), chronic fatigue syndrome, fatigue, including Parkinson's fatigue, multiple sclerosis fatigue, fatigue caused by a sleep disorder or a circadian rhythm disorder, medication-induced parkinsonism (such as neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor), Gilles de la Tourette's syndrome, epilepsy, and dyskinesias [including tremor (such as rest tremor, essential tremor, postural tremor and intention tremor), chorea (such as Sydenham's chorea, Huntington's disease, benign hereditary chorea, neuroacanthocytosis, symptomatic chorea, drug-induced chorea and hemiballism), myoclonus (including generalised myoclonus and focal myoclonus), tics (including simple tics, complex tics and symptomatic tics), restless leg syndrome and dystonia (including generalised dystonia such as iodiopathic dystonia, drug-induced dystonia, symptomatic dystonia and paroxymal dystonia, and focal dystonia such as blepharospasm, oromandibular dystonia, spasmodic dysphonia, spasmodic torticollis, axial dystonia, dystonic writer's cramp and hemiplegic dystonia); attention deficit/hyperactivity disorder (ADHD); conduct disorder; migraine (including migraine headache); urinary incontinence; substance tolerance, substance withdrawal (including, substances such as opiates, nicotine, tobacco products, alcohol, benzodiazepines, cocaine, sedatives, hypnotics, etc.); psychosis; schizophrenia; anxiety (including generalized anxiety disorder, panic disorder, and obsessive compulsive disorder); mood disorders (including depression, mania, bipolar disorders); trigeminal neuralgia; hearing loss; tinnitus; neuronal damage including ocular damage; retinopathy; macular degeneration of the eye; emesis; brain edema; pain, including acute and chronic pain states, severe pain, intractable pain, inflammatory pain, neuropathic pain, post-traumatic pain, bone and joint pain (osteoarthritis), repetitive motion pain, dental pain, cancer pain, myofascial pain (muscular injury, fibromyalgia), perioperative pain (general surgery, gynecological), chronic pain, neuropathic pain, post-traumatic pain, trigeminal neuralgia, migraine and migraine headache.

Thus, in specific embodiments the present invention provides methods for: enhancing the quality of sleep; augmenting sleep maintenance; increasing REM sleep; increasing stage 2 sleep; decreasing fragmentation of sleep patterns; treating insomnia; enhancing cognition; increasing memory retention; treating or controlling obesity; treating or controlling depression; treating, controlling, ameliorating or reducing the risk of epilepsy, including absence epilepsy; treating or controlling pain, including neuropathic pain; treating or controlling Parkinson's disease; treating or controlling psychosis; treating or controlling addiction; treating or controlling depression; or treating, controlling, ameliorating or reducing the risk of schizophrenia, in a mammalian patient in need thereof which comprises administering to the patient a therapeutically effective amount of a compound of the present invention.

The subject compounds are further useful in a method for the prevention, treatment, control, amelioration, or reducation of risk of the diseases, disorders and conditions noted herein. The dosage of active ingredient in the compositions of this invention may be varied, however, it is necessary that the amount of the active ingredient be such that a suitable dosage form is obtained. The active ingredient may be administered to patients (animals and human) in need of such treatment in dosages that will provide optimal pharmaceutical efficacy. The selected dosage depends upon the desired therapeutic effect, on the route of administration, and on the duration of the treatment. The dose will vary from patient to patient depending upon the nature and severity of disease, the patient's weight, special diets then being followed by a patient, concurrent medication, and other factors which those skilled in the art will recognize. Generally, dosage levels of between 0.0001 to 10 mg/kg. of body weight daily are administered to the patient, e.g., humans and elderly humans, to obtain effective antagonism of orexin receptors. The dosage range will generally be about 0.5 mg to 1.0 g. per patient per day which may be administered in single or multiple doses. In one embodiment, the dosage range will be about 0.5 mg to 500 mg per patient per day; in another embodiment about 0.5 mg to 200 mg per patient per day; and in yet another embodiment about 5 mg to 50 mg per patient per day. Pharmaceutical compositions of the present invention may be provided in a solid dosage formulation such as comprising about 0.5 mg to 500 mg active ingredient, or comprising about 1 mg to 250 mg active ingredient. The pharmaceutical composition may be provided in a solid dosage formulation comprising about 1 mg, 5 mg, 10 mg, 25 mg, 50 mg, 100 mg, 200 mg or 250 mg active ingredient. For oral administration, the compositions may be provided in the form of tablets containing 1.0 to 1000 milligrams of the active ingredient, such as 1, 5, 10, 15, 20, 25, 50, 75, 100, 150, 200, 250, 300, 400, 500, 600, 750, 800, 900, and 1000 milligrams of the active ingredient for the symptomatic adjustment of the dosage to the patient to be treated. The compounds may be administered on a regimen of 1 to 4 times per day, such as once or twice per day.

The compounds of the present invention may be used in combination with one or more other drugs in the treatment, prevention, control, amelioration, or reduction of risk of diseases or conditions for which compounds of the present invention or the other drugs may have utility, where the combination of the drugs together are safer or more effective than either drug alone. Such other drug(s) may be administered, by a route and in an amount commonly used therefor, contemporaneously or sequentially with a compound of the present invention. When a compound of the present invention is used contemporaneously with one or more other drugs, a pharmaceutical composition in unit dosage form containing such other drugs and the compound of the present invention is contemplated. However, the combination therapy may also includes therapies in which the compound of the present invention and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of the present invention. The above combinations include combinations of a compound of the present invention not only with one other active compound, but also with two or more other active compounds.

Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is contemplated. Accordingly, the pharmaceutical compositions of the present invention include those that also contain one or more other active ingredients, in addition to a compound of the present invention.

The weight ratio of the compound of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, such as about 200:1 to about 1:200. Combinations of a compound of the present invention and other active ingredients will generally also be within the aforementioned range, but in each case, an effective dose of each active ingredient should be used. In such combinations the compound of the present invention and other active agents may be administered separately or in conjunction. In addition, the administration of one element may be prior to, concurrent to, or subsequent to the administration of other agent(s).

The compounds of the present invention may be administered in combination with other compounds which are known in the art to be useful for enhancing sleep quality and preventing and treating sleep disorders and sleep disturbances, including e.g., sedatives, hypnotics, anxiolytics, antipsychotics, antianxiety agents, antihistamines, benzodiazepines, barbiturates, cyclopyrrolones, GABA agonists, 5HT-2 antagonists including 5HT-2A antagonists and 5HT-2A/2C antagonists, histamine antagonists including histamine H3 antagonists, histamine H3 inverse agonists, imidazopyridines, minor tranquilizers, melatonin agonists and antagonists, melatonergic agents, other orexin antagonists, orexin agonists, prokineticin agonists and antagonists, pyrazolopyrimidines, T-type calcium channel antagonists, triazolopyridines, and the like, such as: adinazolam, allobarbital, alonimid, alprazolam, amitriptyline, amobarbital, amoxapine, armodafinil, APD-125, bentazepam, benzoctamine, brotizolam, bupropion, busprione, butabarbital, butalbital, capromorelin, capuride, carbocloral, chloral betaine, chloral hydrate, chlordiazepoxide, clomipramine, clonazepam, cloperidone, clorazepate, clorethate, clozapine, conazepam, cyprazepam, desipramine, dexclamol, diazepam, dichloralphenazone, divalproex, diphenhydramine, doxepin, EMD-281014, eplivanserin, estazolam, eszopiclone, ethchlorynol, etomidate, fenobam, flunitrazepam, flurazepam, fluvoxamine, fluoxetine, fosazepam, gaboxadol, glutethimide, halazepam, hydroxyzine, ibutamoren, imipramine, indiplon, lithium, lorazepam, lorme azepam, LY-156735, maprotiline, MDL-100907, mecloqualone, melatonin, mephobarbital, meprobamate, methaqualone, methyprylon, midaflur, midazolam, modafinil, nefazodone, NGD-2-73, nisobamate, nitrazepam, nortriptyline, ornortriptyline, oxazepam, paraldehyde, paroxetine, pentobarbital, perlapine, perphenazine, phenelzine, phenobarbital, prazepam, promethazine, propofol, protriptyline, quazepam, ramelteon, reclazepam, roletamide, secobarbital, sertraline, suproclone, TAK-375, temazepam, thioridazine, tiagabine, tracazolate, tranylcypromaine, trazodone, triazolam, trepipam, tricetamide, triclofos, trifluoperazine, trimetozine, trimipramine, uldazepam, venlafaxine, zaleplon, zolazepam, zopiclone, zolpidem, and salts thereof, and combinations thereof, and the like, or the compound of the present invention may be administered in conjunction with the use of physical methods such as with light therapy or electrical stimulation.

In another embodiment, the subject compound may be employed in combination with other compounds which are known in the art, either administered separately or in the same pharmaceutical compositions, include, but are not limited to: insulin sensitizers including (i) PPARγ antagonists such as glitazones (e.g. ciglitazone; darglitazone; englitazone; isaglitazone (MCC-555); pioglitazone; rosiglitazone; troglitazone; tularik; BRL49653; CLX-0921; 5-BTZD), GW-0207, LG-100641, and LY-300512, and the like); (iii) biguanides such as metformin and phenformin; (b) insulin or insulin mimetics, such as biota, LP-100, novarapid, insulin detemir, insulin lispro, insulin glargine, insulin zinc suspension (lente and ultralente); Lys-Pro insulin, GLP-1 (73-7) (insulintropin); and GLP-1 (7-36)-$NH_2$); (c) sulfonylureas, such as acetohexamide; chlorpropamide; diabinese; glibenclamide; glipizide; glyburide; glimepiride; gliclazide; glipentide; gliquidone; glisolamide; tolazamide; and tolbutamide; (d) α-glucosidase inhibitors, such as acarbose, adiposine; camiglibose; emiglitate; miglitol; voglibose; pradimicin-Q; salbostatin; CKD-711; MDL-25,637; MDL-73,945; and MOR 14, and the like; (e) cholesterol lowering agents such as (i) HMG-CoA reductase inhibitors (atorvastatin, itavastatin, fluvastatin, lovastatin, pravastatin, rivastatin; rosuvastatin, simvastatin, and other statins), (ii) bile acid absorbers/sequestrants, such as cholestyramine, colestipol, dialkylaminoalkyl derivatives of a cross-linked dextran; Colestid®; LoCholest®, and the like, (ii) nicotinyl alcohol, nicotinic acid or a salt thereof, (iii) proliferator-activater receptor α agonists such as fenofibric acid derivatives (gemfibrozil, clofibrate, fenofibrate and benzafibrate), (iv) inhibitors of cholesterol absorption such as stanol esters, beta-sitosterol, sterol glycosides such as tiqueside; and azetidinones such as ezetimibe, and the like, and (acyl CoA:cholesterol acyltransferase (ACAT)) inhibitors such as avasimibe, and melinamide, (v) anti-oxidants, such as probucol, (vi) vitamin E, and (vii) thyromimetics; (f) PPARα agonists such as beclofibrate, benzafibrate, ciprofibrate, clofibrate, etofibrate, fenofibrate, and gemfibrozil; and other fibric acid derivatives, such as Atromid®, Lopid® and Tricor®, and the like, and PPARα agonists as described in WO 97/36579; (g) PPARδ agonists, such as those disclosed in WO97/28149; (h) PPAR α/δ agonists, such as muraglitazar, and the compounds disclosed in U.S. Pat. No. 6,414,002; (i) anti-obesity agents, such as (1) growth hormone secretagogues, growth hormone secretagogue receptor agonists/antagonists, such as NN703, hexarelin, MK-0677, SM-130686, CP-424,391, L-692,429, and L-163, 255, and such as those disclosed in U.S. Pat. Nos. 5,536,716, and 6,358,951, U.S. Patent Application Nos. 2002/049196 and 2002/022637, and PCT Application Nos. WO 01/56592 and WO 02/32888; (2) protein tyrosine phosphatase-1B (PTP-1B) inhibitors; (3) cannabinoid receptor ligands, such as cannabinoid $CB_1$ receptor antagonists or inverse agonists, such as rimonabant, taranabant, AMT-251, and SR-14778 and SR 141716A (Sanofi Synthelabo), SLV-319 (Solvay), BAY 65-2520 (Bayer) and those disclosed in U.S. Pat. Nos. 5,532,237, 4,973,587, 5,013,837, 5,081,122, 5,112,820, 5,292,736, 5,624,941, 6,028,084, PCT Application Nos. WO 96/33159, WO 98/33765, WO98/43636, WO98/43635, WO 01/09120, WO98/31227, WO98/41519, WO98/37061, WO00/10967, WO00/10968, WO97/29079, WO99/02499, WO 01/58869, WO 01/64632, WO 01/64633, WO 01/64634, WO02/076949, WO 03/007887, WO 04/048317, and WO 05/000809; (4) anti-obesity serotonergic agents, such as fenfluramine, dexfenfluramine, phentermine, and sibutramine; (5) β3-adrenoreceptor agonists, such as AD9677/TAK677 (Dainippon/Takeda), CL-316,243, SB 418790, BRL-37344, L-796568, BMS-196085, BRL-35135A, CGP12177A, BTA-243, Trecadrine, Zeneca D7114, SR 59119A; (6) pancreatic lipase inhibitors, such as orlistat (Xenical®), Triton WR1339, RHC80267, lipstatin, tetrahydrolipstatin, teasaponin, diethylumbelliferyl phosphate, and those disclosed in PCT Application No. WO 01/77094; (7) neuropeptide Y1 antagonists, such as BIBP3226, J-115814, BIBO 3304, LY-357897, CP-671906, GI-264879A, and those disclosed in U.S. Pat. No. 6,001,836, and PCT Patent Publication Nos. WO 96/14307, WO 01/23387, WO 99/51600, WO 01/85690, WO 01/85098, WO 01/85173, and WO 01/89528; (8) neuropeptide Y5 antagonists, such as GW-569180A, GW-594884A, GW-587081X, GW-548118X, FR226928, FR 240662, FR252384, 1229U91, GI-264879A, CGP71683A, LY-377897, PD-160170, SR-120562A, SR-120819A and JCF-104, and those disclosed in U.S. Pat. Nos. 6,057,335; 6,043,246; 6,140,354; 6,166,038; 6,180,653; 6,191,160; 6,313,298; 6,335,345; 6,337,332; 6,326,375; 6,329,395; 6,340,683; 6,388,077; 6,462,053; 6,649,624; and 6,723,847, European Patent Nos. EP-01010691, and EP-01044970; and PCT International Patent Publication Nos. WO 97/19682, WO 97/20820, WO 97/20821, WO 97/20822, WO 97/20823, WO 98/24768; WO 98/25907; WO 98/25908; WO 98/27063, WO 98/47505; WO 98/40356; WO 99/15516; WO 99/27965; WO 00/64880, WO 00/68197, WO 00/69849, WO 01/09120, WO 01/14376; WO 01/85714, WO 01/85730, WO 01/07409, WO 01/02379, WO 01/02379, WO 01/23388, WO 01/23389, WO 01/44201, WO 01/62737, WO 01/62738, WO 01/09120, WO 02/22592, WO 0248152, and WO 02/49648; WO 02/094825; WO 03/014083; WO 03/10191; WO 03/092889; WO 04/002986; and WO 04/031175; (9) melanin-concentrating hormone (MCH) receptor antagonists, such as those disclosed in WO 01/21577 and WO 01/21169; (10) melanin-concentrating hormone 1 receptor (MCH1R) antagonists, such as T-226296 (Takeda), and those disclosed in PCT Patent Application Nos. WO 01/82925, WO 01/87834, WO 02/051809, WO 02/06245, WO 02/076929, WO 02/076947, WO 02/04433, WO 02/51809, WO 02/083134, WO 02/094799, WO 03/004027; (11) melanin-concentrating hormone 2 receptor (MCH$_2$R) agonist/antagonists; (12) orexin receptor antagonists, such as SB-334867-A, and those disclosed in patent publications herein; (13) serotonin reuptake inhibitors such as fluoxetine, paroxetine, and sertraline; (14) melanocortin agonists, such as Melanotan II; (15) Mc4r (melanocortin 4 receptor) agonists, such as CHIR86036 (Chiron), ME-10142, and ME-10145 (Melacure), CHIR86036 (Chiron); PT-141, and PT-14 (Palatin); (16) 5HT-2 agonists; (17) 5HT2C (serotonin receptor 2C) agonists, such as BVT933, DPCA37215, WAY161503, R-1065, and those disclosed in U.S. Pat. No. 3,914,250, and PCT Application Nos. WO 02/36596, WO 02/48124, WO 02/10169, WO 01/66548, WO 02/44152, WO 02/51844, WO 02/40456, and WO 02/40457; (18) galanin antagonists; (19) CCK agonists; (20) CCK-A (cholecystokinin-A) agonists, such as AR-R 15849, GI 181771, JMV-180, A-71378, A-71623 and SR14613, and those discribed in U.S. Pat. No. 5,739,106; (21) GLP-1 agonists; (22) corticotropin-releasing hormone agonists; (23) histamine receptor-3 (H3) modulators; (24) histamine receptor-3 (H3) antagonists/inverse agonists, such as hioperamide, 3-(1H-imidazol-4-yl)propyl N-(4-pentenyl)carbamate, clobenpropit, iodophenpropit, imoproxifan, GT2394 (Gliatech), and O-[3-(1H-imidazol-4-yl)propanol]-carbamates; (25) β-hydroxy steroid dehydrogenase-1 inhibitors (β-HSD-1); (26) PDE (phosphodiesterase) inhibitors, such as theophylline, pentoxifylline, zaprinast, sildenafil, aminone, milrinone, cilostamide, rolipram, and cilomilast; (27) phosphodiesterase-3B (PDE3B) inhibitors; (28) NE (norepinephrine) transport inhibitors, such as GW 320659, despiramine, talsupram, and nomifensine; (29) ghrelin receptor antagonists, such as those disclosed in PCT Application Nos. WO 01/87335, and WO 02/08250; (30) leptin, including recombinant human leptin (PEG-OB, Hoffman La Roche) and recombinant methionyl human leptin (Amgen); (31) leptin derivatives; (32) BRS3 (bombesin receptor subtype 3) agonists such as [D-Phe6,beta-Ala11,Phe13,Nle14]Bn(6-14) and [D-Phe6,Phe13]Bn(6-13)propylamide, and those compounds disclosed in Pept. Sci. 2002 August; 8(8): 461-75); (33) CNTF (Ciliary neurotrophic factors), such as GI-181771 (Glaxo-SmithKline), SR146131 (Sanofi Synthelabo), butabindide, PD 170,292, and PD 149164 (Pfizer); (34) CNTF derivatives, such as axokine (Regeneron); (35) monoamine reuptake inhibitors, such as sibutramine; (36) UCP-1 (uncoupling protein-1), 2, or 3 activators, such as phytanic acid, 4-[(E)-2-(5,6,7,8-tetrahydro-5,5,8,8-tetramethyl-2-napthalenyl)-1-propenyl]benzoic acid (TTNPB), retinoic acid; (37) thyroid hormone β agonists, such as KB-2611 (KaroBioBMS); (38) FAS (fatty acid synthase) inhibitors, such as Cerulenin and C75; (39) DGAT1 (diacylglycerol acyltransferase 1) inhibitors; (40) DGAT2 (diacylglycerol acyltransferase 2) inhibitors; (41) ACC2 (acetyl-CoA carboxylase-2) inhibitors; (42) glucocorticoid antagonists; (43) acyl-estrogens, such as oleoyl-estrone, disclosed in del Mar-Grasa, M. et al., Obesity Research, 9:202-9 (2001); (44) dipeptidyl peptidase IV (DP-IV) inhibitors, such as isoleucine thiazolidide, valine pyrrolidide, NVP-DPP728, LAF237, P93/01, TSL 225, TMC-2A/2B/2C, FE 999011, P9310/K364, VIP 0177, SDZ 274-444, sitagliptin; and the compounds disclosed in U.S. Pat. No. 6,699,871, WO 03/004498; WO 03/004496; EP 1 258 476; WO 02/083128; WO 02/062764; WO 03/000250; WO 03/002530; WO 03/002531; WO 03/002553; WO 03/002593; WO 03/000180; and WO 03/000181; (46) dicarboxylate transporter inhibitors; (47) glucose transporter inhibitors; (48) phosphate transporter inhibitors; (49) Metformin (Glucophage®); (50) Topiramate (Topimax®); (50) peptide YY, PYY 3-36, peptide YY analogs, derivatives, and fragments such as BIM-43073D, BIM-43004C (Olitvak, D. A. et al., Dig. Dis. Sci. 44(3):643-48 (1999)); (51) Neuropeptide Y2 (NPY2) receptor agonists such NPY3-36, N acetyl [Leu(28,31)] NPY 24-36, TASP-V, and cyclo-(28/32)-Ac-[Lys28-Glu32]-(25-36)-pNPY; (52) Neuropeptide Y4 (NPY4) agonists such as pancreatic peptide (PP), and other Y4 agonists such as 1229U91; (54) cyclooxygenase-2 inhibitors such as etoricoxib, celecoxib, valdecoxib, parecoxib, lumiracoxib, BMS347070, tiracoxib or JTE522, ABT963, CS502 and GW406381; (55) Neuropeptide Y1 (NPY1) antagonists such as BIBP3226, J-115814, BIBO 3304, LY-357897, CP-671906, GI-264879A; (56) Opioid antagonists such as nalmefene (Revex®), 3-methoxynaltrexone, naloxone, naltrexone; (57) 11β HSD-1 (11-beta hydroxy steroid dehydrogenase type 1) inhibitors such as BVT 3498, BVT 2733, and those disclosed in WO 01/90091, WO 01/90090, WO 01/90092, U.S. Pat. No. 6,730,690 and US 2004-0133011; (58) a minorex; (59) amphechloral; (60) amphetamine; (61) benzphetamine; (62) chlorphentermine; (63) clobenzorex; (64) cloforex; (65) clominorex; (66) clortermine; (67) cyclexedrine; (68) dextroamphetamine; (69) diphemethoxidine, (70) N-ethylamphetamine; (71) fenbutrazate; (72) fenisorex; (73) fenproporex; (74) fludorex; (75) fluminorex; (76) furfurylmethylamphetamine; (77) levamfetamine; (78) levophacetoperane; (79) mefenorex; (80) metamfepramone; (81) methamphetamine; (82) norpseudoephedrine; (83) pentorex; (84) phendimetrazine; (85) phenmetrazine; (86) picilorex; (87) phytopharm 57; and (88) zonisamide; (89) neuromedin U and analogs or derivatives thereof, (90) oxyntomodulin and analogs or derivatives thereof, and (91) Neurokinin-1 receptor antagonists (NK-1 antagonists) such as the compounds disclosed in: U.S. Pat. Nos. 5,162,339, 5,232,929, 5,242,930, 5,373,003, 5,387,595, 5,459,270, 5,494,926, 5,496,833, and 5,637,699.

In another embodiment, the subject compound may be employed in combination with an anti-depressant or anti-anxiety agent, including norepinephrine reuptake inhibitors (including tertiary amine tricyclics and secondary amine tricyclics), selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists, neurokinin-1 receptor antagonists, atypical anti-depressants, benzodiazepines, 5-HT$_{1A}$ agonists or antagonists, especially 5-HT$_{1A}$ partial agonists, and corticotropin releasing factor (CRF) antagonists. Specific agents include: amitriptyline, clomipramine, doxepin, imipramine and trimipramine; amoxapine, desipramine, maprotiline, nortriptyline and protriptyline; citalopram, duloxetine, fluoxetine, fluvoxamine, paroxetine and sertraline; isocarboxazid, phenelzine, tranylcypromine and selegiline; moclobemide: venlafaxine; aprepitant; bupropion, lithium, nefazodone, trazodone and viloxazine; alprazolam, chlordiazepoxide, clonazepam, chlorazepate, diazepam, halazepam, lorazepam, oxazepam and prazepam; buspirone, flesinoxan, gepirone and ipsapirone, and pharmaceutically acceptable salts thereof.

In another embodiment, the subject compound may be employed in combination with anti-Alzheimer's agents; beta-secretase inhibitors; gamma-secretase inhibitors; growth hormone secretagogues; recombinant growth hormone; HMG-CoA reductase inhibitors; NSAID's including ibuprofen; vitamin E; anti-amyloid antibodies; CB-1 receptor antagonists or CB-1 receptor inverse agonists; antibiotics such as doxycycline and rifampin; N-methyl-D-aspartate (NMDA) receptor antagonists, such as memantine; cholinesterase inhibitors such as galantamine, rivastigmine, donepezil, and tacrine; growth hormone secretagogues such as ibutamoren, ibutamoren mesylate, and capromorelin; histamine $H_3$ antagonists; AMPA agonists; PDE IV inhibitors; GABA$_A$ inverse agonists; or neuronal nicotinic agonists.

In another embodiment, the subject compound may be employed in combination with sedatives, hypnotics, anxiolytics, antipsychotics, antianxiety agents, cyclopyrrolones, imidazopyridines, pyrazolopyrimidines, minor tranquilizers, melatonin agonists and antagonists, melatonergic agents, benzodiazepines, barbiturates, 5HT-2 antagonists, and the like, such as: adinazolam, allobarbital, alonimid, alprazolam, amitriptyline, amobarbital, amoxapine, bentazepam, benzoctamine, brotizolam, bupropion, busprione, butabarbital, butalbital, capuride, carbocloral, chloral betaine, chloral hydrate, chlordiazepoxide, clomipramine, clonazepam, cloperidone, clorazepate, clorethate, clozapine, cyprazepam, desipramine, dexclamol, diazepam, dichloralphenazone, divalproex, diphenhydramine, doxepin, estazolam, ethchlorvynol, etomidate, fenobam, flunitrazepam, flurazepam, fluvoxamine, fluoxetine, fosazepam, glutethimide, halazepam, hydroxyzine, imipramine, lithium, lorazepam, lormetazepam, maprotiline, mecloqualone, melatonin, mephobarbital, meprobamate, methaqualone, midaflur, midazolam, nefazodone, nisobamate, nitrazepam, nortriptyline, oxazepam, paraldehyde, paroxetine, pentobarbital, perlapine, perphenazine, phenelzine, phenobarbital, prazepam, promethazine, propofol, protriptyline, quazepam, reclazepam, roletamide, secobarbital, sertraline, suproclone, temazepam, thioridazine, tracazolate, tranylcypromaine, trazodone, triazolam, trepipam, tricetamide, triclofos, trifluoperazine, trimetozine, trimipramine, uldazepam, venlafaxine, zaleplon, zolazepam, zolpidem, and salts thereof, and combinations thereof, and the like, or the subject compound may be administered in conjunction with the use of physical methods such as with light therapy or electrical stimulation.

In another embodiment, the subject compound may be employed in combination with levodopa (with or without a selective extracerebral decarboxylase inhibitor such as carbidopa or benserazide), anticholinergics such as biperiden (optionally as its hydrochloride or lactate salt) and trihexyphenidyl (benzhexyl) hydrochloride, COMT inhibitors such as entacapone, MOA-B inhibitors, antioxidants, A2a adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and pramipexole.

In another embodiment, the subject compound may be employed in combination with acetophenazine, alentemol, benzhexyl, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, risperidone, sulpiride, tetrabenazine, trihexyphenidyl, thioridazine, thiothixene or trifluoperazine.

In another embodiment, the subject compound may be employed in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone.

In another embodiment, the subject compound may be employed in combination with a nicotine agonist or a nicotine receptor partial agonist such as varenicline, opioid antagonists (e.g., naltrexone (including naltrexone depot), antabuse, and nalmefene), dopaminergic agents (e.g., apomorphine), ADD/ADHD agents (e.g., methylphenidate hydrochloride (e.g., Ritalin® and Concerta®), atomoxetine (e.g., Strattera®), a monoamine oxidase inhibitor (MAOI), amphetamines (e.g., Adderall®) and anti-obesity agents, such as apo-B/MTP inhibitors, 11Beta-hydroxy steroid dehydrogenase-1 (11Beta-HSD type 1) inhibitors, peptide YY3-36 or analogs thereof, MCR-4 agonists, CCK-A agonists, monoamine reuptake inhibitors, sympathomimetic agents, β3 adrenergic receptor agonists, dopamine receptor agonists, melanocyte-stimulating hormone receptor analogs, 5-HT2c receptor agonists, melanin concentrating hormone receptor antagonists, leptin, leptin analogs, leptin receptor agonists, galanin receptor antagonists, lipase inhibitors, bombesin receptor agonists, neuropeptide-Y receptor antagonists (e.g., NPY Y5 receptor antagonists), thyromimetic agents, dehydroepiandrosterone or analogs thereof, glucocorticoid receptor antagonists, other orexin receptor antagonists, glucagon-like peptide-1 receptor agonists, ciliary neurotrophic factors, human agouti-related protein antagonists, ghrelin receptor antagonists, histamine 3 receptor antagonists or inverse agonists, and neuromedin U receptor agonists, and pharmaceutically acceptble salts thereof.

In another embodiment, the subject compound may be employed in combination with an anoretic agent such as a minorex, amphechloral, amphetamine, benzphetamine, chlorphentermine, clobenzorex, cloforex, clominorex, clortermine, cyclexedrine, dexfenfluramine, dextroamphetamine, diethylpropion, diphemethoxidine, N-ethylamphetamine, fenbutrazate, fenfluramine, fenisorex, fenproporex, fludorex, fluminorex, furfurylmethylamphetamine, levamfetamine, levophacetoperane, mazindol, mefenorex, metamfepramone, methamphetamine, norpseudoephedrine, pentorex, phendimetrazine, phenmetrazine, phentermine, phenylpropanolamine, picilorex and sibutramine; selective serotonin reuptake inhibitor (SSRI); halogenated amphetamine derivatives, including chlorphentermine, cloforex, clortermine, dexfenfluramine, fenfluramine, picilorex and sibutramine; and pharmaceutically acceptble salts thereof.

In another embodiment, the subject compound may be employed in combination with an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non-steroidal antiinflammatory agent, or a cytokine-suppressing antiinflammatory agent, for example with a compound such as acetaminophen, asprin, codiene, fentanyl, ibuprofen, indomethacin, ketorolac, morphine, naproxen, phenacetin, piroxicam, a steroidal analgesic, sufentanyl, sunlindac, tenidap, and the like. Similarly, the subject compound may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levo-desoxy-ephedrine;

an antitussive such as codeine, hydrocodone, caramiphen, carbetapentane, or dextramethorphan; a diuretic; and a sedating or non-sedating antihistamine.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans. The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. Compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Aqueous suspensions contain the active materials in admixture with excipients suitable for the manufacture of aqueous suspensions. Oily suspensions may be formulated by suspending the active ingredient in a suitable oil. Oil-in-water emulsions may also be employed. Dispersible powders and granules suitable for preparation of an aqueous suspension by the addition of water provide the active ingredient in admixture with a dispersing or wetting agent, suspending agent and one or more preservatives. Pharmaceutical compositions of the present compounds may be in the form of a sterile injectable aqueous or oleagenous suspension. The compounds of the present invention may also be administered in the form of suppositories for rectal administration. For topical use, creams, ointments, jellies, solutions or suspensions, etc., containing the compounds of the present invention may be employed. The compounds of the present invention may also be formulated for administered by inhalation. The compounds of the present invention may also be administered by a transdermal patch by methods known in the art.

Several methods for preparing the compounds of this invention are illustrated in the following Schemes and Examples. Starting materials are made according to procedures known in the art or as illustrated herein. The following abbreviations are used herein: Me: methyl; Et: ethyl; t-Bu: tert-butyl; Ar: aryl; Ph: phenyl; Bn: benzyl; Ac: acetyl; THF: tetrahydrofuran; DEAD: diethylazodicarboxylate; DIPEA: N,N-diisopropylethylamine; DMSO: dimethylsulfoxide; EDC: N-(3-Dimethylaminopropyl)-N'-ethylcarbodiimide; HOBT: hydroxybenzotriazole hydrate; Boc: tert-butyloxy carbonyl; Et$_3$N: triethylamine; DCM: dichloromethane; DCE: dichloroethane; BSA: bovine serum albumin; TFA: trifluoracetic acid; DMF: N,N-dimethylformamide; MTBE: methyl tert-butyl ether; PyClu: 1-(chloro-1-pyrrolidinylmethylene)-pyrrolidinium hexafluorophosphate; SOCl$_2$: thionyl chloride; CDI: carbonyl diimidazole; rt: room temperature; HPLC: high performance liquid chromatography. The compounds of the present invention can be prepared in a variety of fashions.

In some cases the final product may be further modified, for example, by manipulation of substituents. These manipulations may include, but are not limited to, reduction, oxidation, alkylation, acylation, and hydrolysis reactions which are commonly known to those skilled in the art. In some cases the order of carrying out the foregoing reaction schemes may be varied to facilitate the reaction or to avoid unwanted reaction products. The following examples are provided so that the invention might be more fully understood. These examples are illustrative only and should not be construed as limiting the invention in any way.

SCHEME A

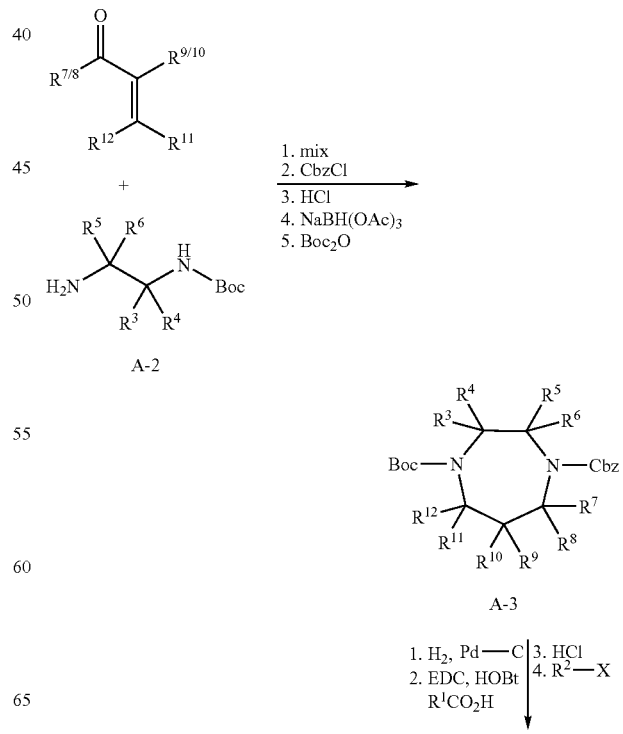

-continued

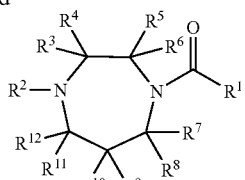

A-4

Unsaturated ketones are reacted with differentially protected ethylenediamines in a Michael reaction and subsequently protected as Cbz carbamates. The Boc protecting group is then be deprotected, the resulting amine engaged in a reductive amination reaction, and reprotected to give compounds such as A-3. Intermediates such as A-3 are transformed into final compounds, A-4, through Cbz deprotection, amide formation, Boc deprotection, and finally $S_NAr$ with various heterocycles.

SCHEME B

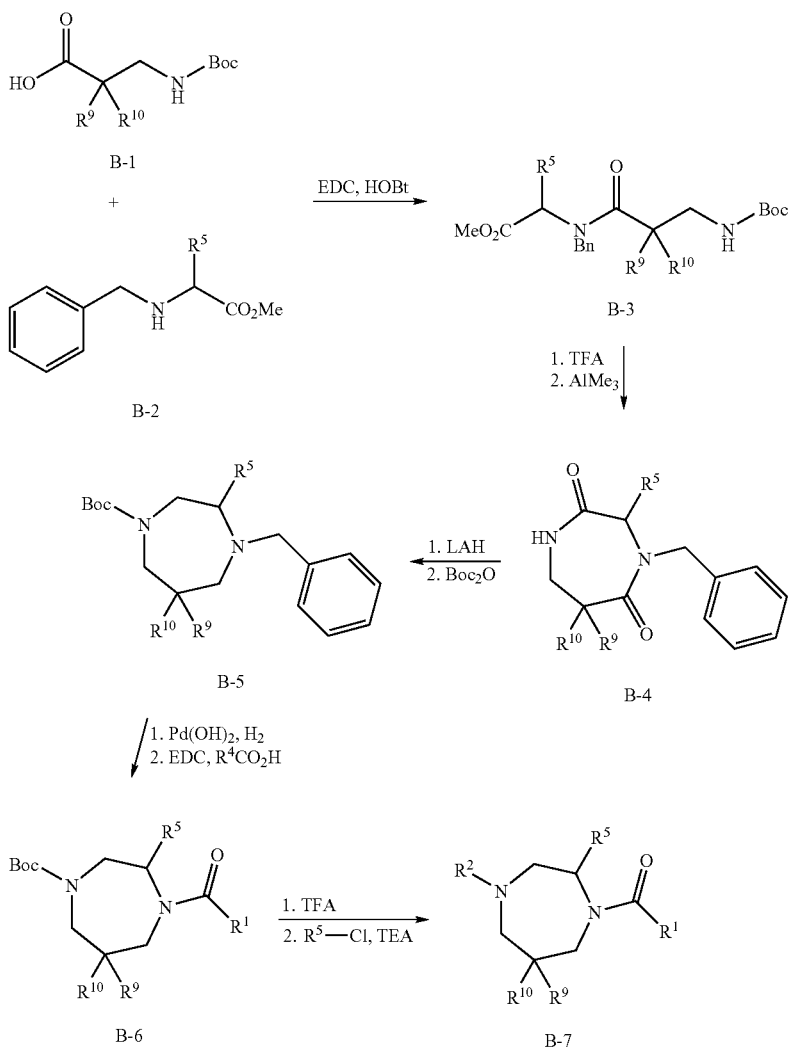

Boc-protected beta-amino acids (B-1) are coupled with benzyl-protected alanine derivatives (B-2) under standard amide coupling conditions to give B-3. Compounds such as B-3 are deprotected and cyclized using TFA followed by trimethylaluminum to afford compounds such as B-4. Reduction with lithium aluminum hydride and Boc protection gives differentially protected compounds B-5. The benzyl group is removed via hydrogenation and coupled with various carboxylic acids to give B-6. These intermediates are advanced to final compounds (b-7) through Boc deprotection and $S_NAr$ chemistry.

Example 1-A

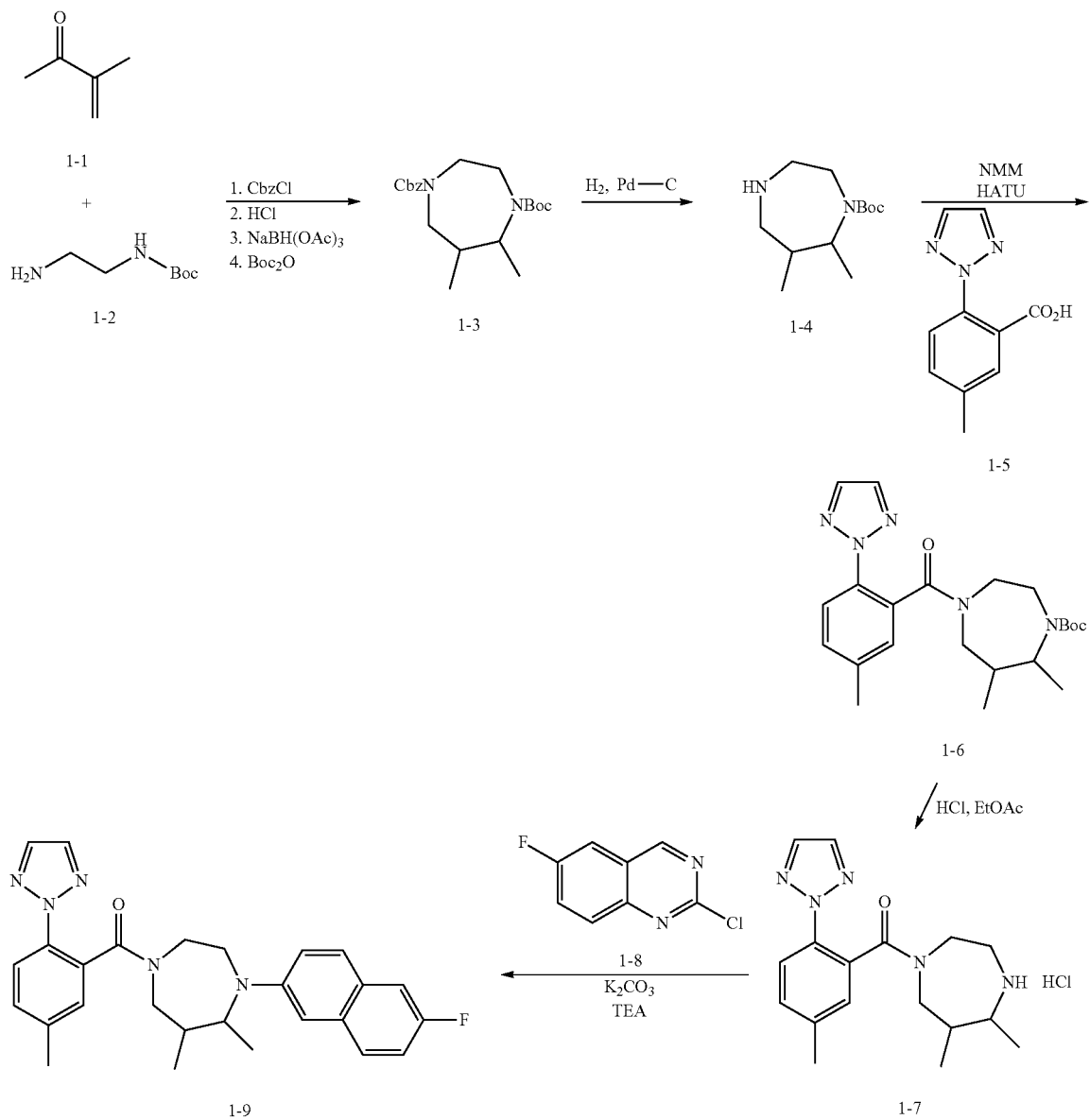

1-benzyl 4-tert-butyl 5,6-dimethyl-1,4-diazepane-1,4-dicarboxylate (1-3)

To a solution of N-Boc-ethylenediamine (5.0 g, 31.2 mmol, 1.0 equiv, 1-2) in diethyl ether (30 mL) was added 3-methyl-3-butene-2-one (2.6 g, 31.2 mmol, 1.0 equiv, 1-1) and the reaction was stirred at room temperature for 18 hours. The reaction mixture was then cooled to 0° C. and triethylamine (6.5 mL, 46.8 mmol, 1.5 equiv) and benzyl chloroformate (5.4 mL, 37.4 mmol, 1.2 equiv) were added. The reaction mixture was stirred a further 12 h and partitioned between EtOAc and a 10% aqueous citric acid solution. The layers were separated and the organic was washed with 5% aqueous $Na_2CO_3$, then with brine, dried over $Na_2SO_4$ and concentrated by rotary evaporation. The residue was dissolved in dioxane (50 mL) and treated with a solution of 4N HCl in dioxane (70 mL, ca. 10 equiv) and the reaction mixture was stirred for 2 h at ambient temperature. The reaction mixture was concentrated directly, dissolved in 1N HCl (100 mL) and extracted with diethyl ether. The aqueous was neutralized with 1N NaOH (150 mL) and subsequently extracted with 3:1 chloroform:ethanol (3×200 mL), dried over $MgSO_4$ and concentrated. The resulting residue was dissolved in DCM (100 mL) and glacial acetic acid (2 mL) was added. After 30 minutes, $NaBH(OAc)_3$ (6.4 g, 30.2 mmol) was added and the reaction was stirred for 1 h. The reaction mixture was concentrated directly; partitioned between saturated $NaHCO_3$ (50 mL) and 3:1 chloroform:ethanol (150 mL) The aqueous layer was extracted with chloroform:ethanol (2×150 mL), dried over $MgSO_4$ and concentrated. The residue was dissolved in DCM (100 mL) and to the solution was added triethylamine (4.2 mL, 30.2 mmol) and $Boc_2O$ (5.0 g, 22.7 mmol) and the reaction mixture was stirred 18 hours. To the reaction mixture was added a 10% aqueous citric acid solution. The organic phase was dried over MgSO$_4$ and concentrated. The residue was purified by column chromatography on silica gel (0 to 75% EtOAc in hexanes) to provide 1-3 as an oil. Data for 1-3: LC/MS: m/z (M+Na)=385.2 found; 385.5 required.

tert-butyl 6,7-dimethyl-1,4-diazepane-1-carboxylate (1-4)

To a solution of 1-3 (3.3 g, 9.1 mmol) in ethyl acetate (45 mL) was added 20% palladium hydroxide on carbon (256 mg) and the reaction was stirred at room temperature under balloon pressure of hydrogen gas overnight. The reaction was filtered through celite and concentrated in vacuo to afford 1-4.

tert-butyl 6,7-dimethyl-4-[5-methyl-2-(2H-1,2,3-triazol-2-yl)benzoyl]-1,4-diazepane-1-carboxylate (1-6)

Compound 1-4 (250 mg, 1.1 mmol), was dissolved in DMF (5 mL) and to this solution was added the carboxylic acid 1-5 (222 mg, 1.1 mmol; see example 1-C), HATU (541 mg, 1.42 mmol) and N-methylmorpholine (602 uL, 5.47 mmol). The reaction stirred at room temperature for 45 minutes, diluted with ethyl acetate and washed with a saturated sodium bicarbonate solution and brine. The organic layer was concentrated and the residue was purified by column chromatography on silica gel (0 to 100% EtOAc in hexanes) to provide 1-6. Data for 1-6: LC/MS: m/z (M-Boc+Na)=314.3 found; 314.5 calculated 5,6-dimethyl-1-[5-methyl-2-(2H-1,2,3-triazol-2-yl)benzoyl]-1,4-diazepane hydrochloride (1-7)

Hydrogen chloride gas was bubbled through a 0° C. solution of the compound 1-6 (385 mg, 0.93 mmol) in ethyl acetate (5 mL) for 1 minute. The reaction was sealed and stirred for 40 minutes. Concentration in vacuo gave the titled compound as a white solid. Data for 1-7: LC/MS: m/z (M+Na)=314.2 found; 314.4 calculated.

2-{6,7-dimethyl-4-[5-methyl-2-(2H-1,2,3-triazol-2-yl)benzoyl]-1,4-diazepan-1-yl}-6-fluoroquinazoline (1-9)

Compound 1-7 (75 mg, 0.21 mmol) was combined with 2-chloro-6-fluoroquinazoline 1-8 (39 mg, 0.21 mmol; see example 1-D), triethylamine (30 uL, 0.21 mmol), and potassium carbonate (296 mg, 2.1 mmol) in toluene (2 mL) and heated in a sealed tube to 130° C. overnight. The reaction was concentrated in vacuo and the residue purified by reverse phase preparative chromatography on a C-18 column (5 to 75% acetonitrile in water with 0.1% TFA buffer). The clean fractions were combined and made basic with 20% sodium carbonate solution. This was extracted with ethyl acetate two times and the combined organics washed with brine and dried with sodium sulfate. Concentration in vacuo gave the titled compound as a solid. Data for 1-9: LC/MS: m/z (M+Na)= 460.2 found; 460.5 calculated.

Example 1-B

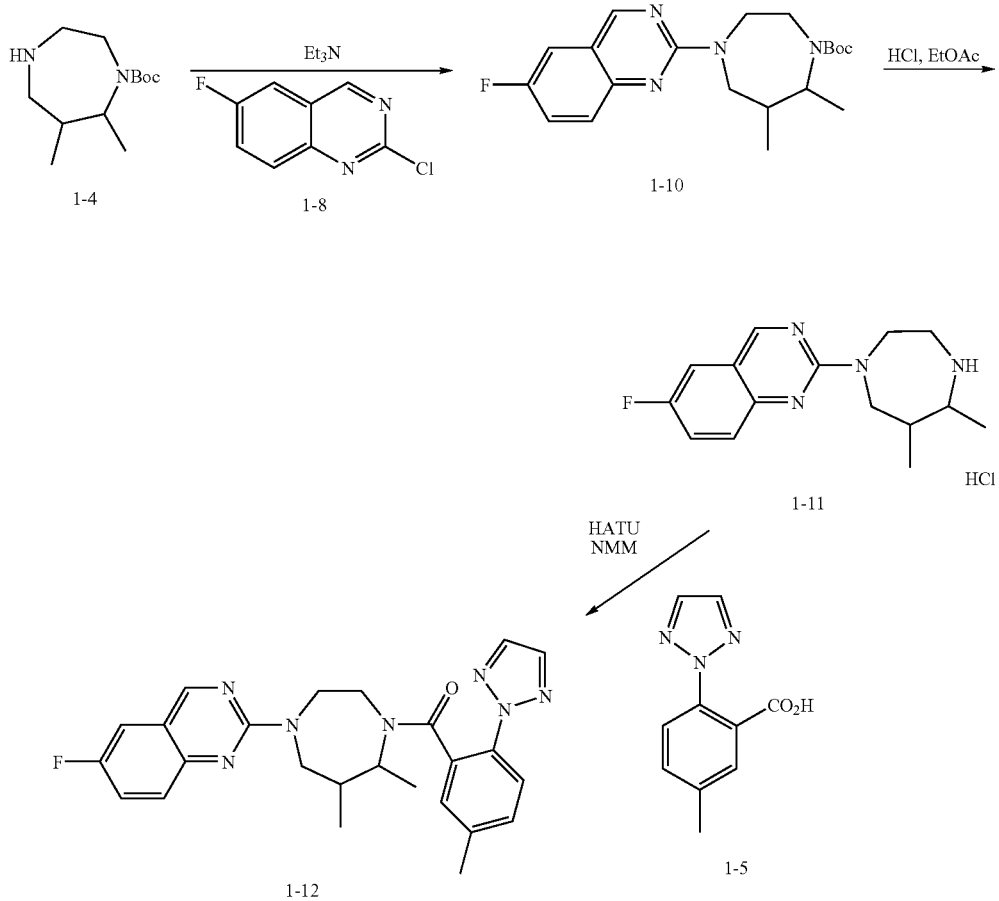

tert-butyl 4-(6-fluoroquinazolin-2-yl)-6,7-dimethyl-1,4-diazepane-1-carboxylate (1-10)

The amine 1-4 (270 mg, 1.18 mmol) was combined with 2-chloro-6-fluoroquinazoline 1-8 (216 mg, 1.18 mmol; see example 1-D), and triethylamine (412 uL, 2.96 mmol), in DMF (5 mL) and heated to 130° C. for 3 hours. The reaction was diluted with EtOAc, washed with saturated sodium bicarbonate solution and brine and the organic layer concentrated in vacuo and the residue was purified by column chromatography on silica gel (0 to 100% EtOAc in hexanes) to provide 1-10. Data for 1-10: LC/MS: m/z (M+Na)=375.2 found; 375.4 calculated.

2-(5,6-dimethyl-1,4-diazepan-1-yl)-6-fluoroquinazoline (1-11)

Hydrogen chloride gas was bubbled through a 0° C. solution of compound 1-10 (338 mg, 0.9 mmol) in ethyl acetate (5 mL) for 1 minute. The reaction was sealed and stirred for 40 minutes. Concentration in vacuo gave the titled compound as a white solid. Data for 1-11: LC/MS: m/z (M+CH$_3$CN)=315.2 found; 315.3 calculated.

2-{5,6-dimethyl-4-[5-methyl-2-(2H-1,2,3-triazol-2-yl)benzoyl]-1,4-diazepan-1-yl}-6-fluoroquinazoline (1-12)

Compound 1-11 (65 mg, 0.21 mmol), was dissolved in DMF (1.5 mL) and to this solution was added 1-5 (42 mg, 0.21 mmol; see example 1-C), HATU (103 mg, 0.27 mmol) and N-methylmorpholine (115 uL, 1.05 mmol). The reaction stirred at room temperature for 1 hour. The reaction was filtered and purified by reverse phase preparative chromatography on a C-18 column (5 to 60% acetonitrile in water with 0.1% TFA buffer). The clean fractions were combined and made basic with 20% sodium carbonate solution. This was extracted with ethyl acetate two times and the combined organics washed with brine and dried with sodium sulfate. Concentration in vacuo gave the titled compound as a solid. Data for 1-12: LC/MS: m/z (M+Na)=460.1 found; 460.5 calculated.

Example 1-C

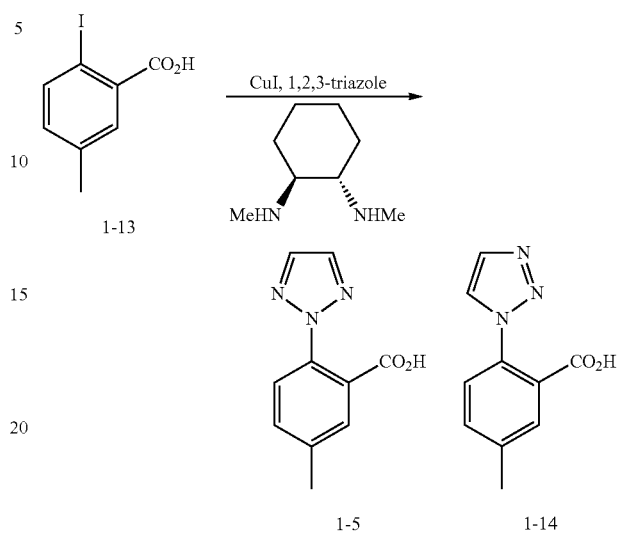

2-(2H-1,2,3-triazol-2-yl)-5-methylbenzoic acid (1-5)

A solution of 2-iodo-5-methylbenzoic acid (1-13, 4.0 g, 15.3 mmol) in DMF (10 mL) was treated with 1,2,3-triazole (2.1 g, 30.5 mmol), CsCO$_3$ (9.95 g, 30.5 mmol), CuI (0.145 g, 0.76 mmol) and trans-N,N'-dimethylcyclohexane-1,2-diamine (0.43 g, 3.05 mmol). The mixture was heated at 120° C. for 10 min in a microwave reactor. The reaction was cooled to room temperature, diluted with water, and washed with EtOAc. The aqueous phase was acidified with 1N HCl and extracted with EtOAc. The organic layer was dried over Na$_2$SO$_4$, filtered and concentrated. The residue was purified by gradient elution on SiO$_2$ (0 to 10% MeOH in water with 0.1% AcOH) to give the faster eluting 2-(2H-1,2,3-triazol-2-yl)-5-methylbenzoic acid 1-5, followed by the undesired regioisomer isomer, 1-(2H-1,2,3-triazol-2-yl)-5-methylbenzoic acid (1-14). Data for 1-5: $^1$HNMR (500 MHz, DMSO-d$_6$) δ 12.98 (br s, 1H), 8.04 (s, 2H), 7.72-7.45 (m, 3H), 2.41 (s, 3H) ppm.

Example 1-D

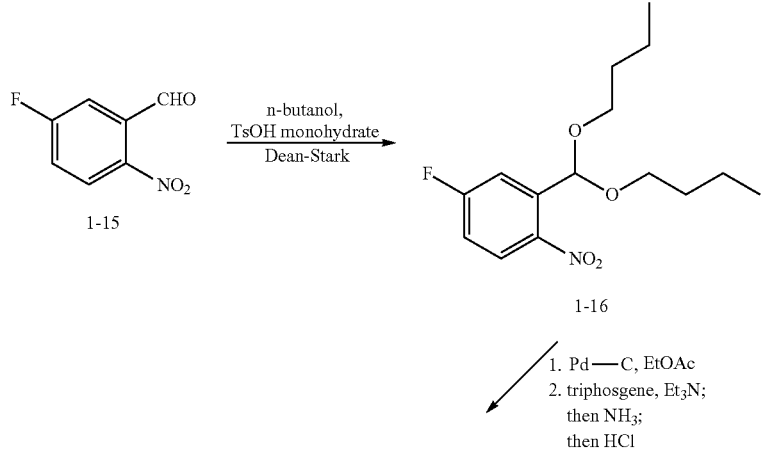

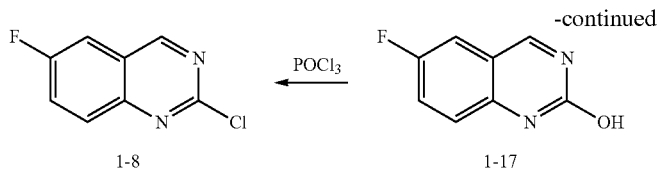

2-(dibutoxymethyl)-4-fluoro-1-nitrobenzene (1-16)

A solution of 5-fluoro-2-nitrobenzaldehyde (1-15, 75 g, 443 mmol), para-toluenesulfonic acid monohydrate (8.4 g, 44.3 mmol), and n-butanol (122 mL, 1.33 mol) was refluxed in toluene (630 mL) using a Dean-Stark apparatus for 15 h. The reaction was cooled, concentrated and partitioned between water (1 L) and EtOAc (1 L). The organic layer was washed with water (1 L) and brine (1 L), dried over $Na_2SO_4$ and concentrated. The crude reaction was purified by column chromatography (0 to 25% EtOAc in hexanes, 1% triethylamine buffer) to yield the 2-(dibutoxymethyl)-4-fluoro-1-nitrobenzene (1-16) as an oil. Data for 1-16: $^1$H NMR (500 MHz, $CDCl_3$) δ 7.92 (dd, J=8.5, 4.5 Hz, 1H), 7.54 (dd, J=9.0, 3.0 Hz, 1H), 7.15-7.11 (m, 1H), 6.05 (s, 1H), 3.67-3.52 (m, 4H), 1.63-1.57 (m, 4H), 1.43-1.35 (m, 4H), 0.94-0.91 (m, 6H) ppm; ESI MS [M+H] for $C_{15}H_{22}FNO_4$ (-acetal)=169.8.

2-chloro-6-fluoroquinazoline (1-8)

To a solution of 2-(dibutoxymethyl)-4-fluoro-1-nitrobenzene (1-16) (26.1 g, 87 mmol) in EtOAc (350 mL) under nitrogen atmosphere at 25° C. was added Pd—C (10 wt %, 2.3 g) and the reaction was placed under hydrogen atmosphere (1 atm). The reaction was stirred for 12 h, filtered through celite and concentrated. The residue was redissolved in THF (350 mL) and cooled to 0° C. To this solution was added triethylamine (45.0 mL, 323 mmol) and triphosgene (8.6 g, 29.1 mmol) in THF (60 mL) dropwise. The reaction was stirred for 10 minutes and ammonia in methanol (46.1 mL, 323 mmol, 7M solution) was added. The reaction was stirred at 0° C. for 10 minutes and quickly warmed to ambient temperature. After 15 minutes at room temperature, the reaction was acidified with 4M HCl in dioxane (120 mL) to pH 2. The reaction was stirred at room temperature for 1 hour and concentrated directly. The residue was azeotroped with toluene and methanol to give a yellow cake (1-17, 6-fluoroquinazolin-2-ol; ESI MS [M+H] for $C_8H_5FN_2O$=164.9). The yellow cake was dissolved in neat phosphorous oxychloride (130 mL) and refluxed (120° C.) for 1 hour. The reaction was cooled and the excess solvent was removed in vaccuo. The crude reaction mixture was dissolved in EtOAc (600 mL) and quenched slowly at 0° C. with water (500 mL). The aqueous phase was extracted with EtOAc (2×200 mL) and the combined organic phase was dried over $MgSO_4$ and concentrated. The crude reaction was purified by column chromatography (0 to 20% EtOAc in dichloromethane) to afford 1-8 as an off-white solid. Data for 1-8: $^1$HNMR (500 MHz, $CDCl_3$) δ 9.29 (s, 1H), 8.04 (dd, J=9.0, 5.0 Hz, 1H), 7.77-7.72 (m, 1H), 7.59 (dd, J=7.5, 2.5 Hz, 1H) ppm; ESI MS [M+H] for $C_8H_4ClFN_2$=183.2.

Example 2

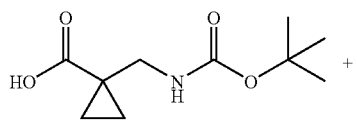

+

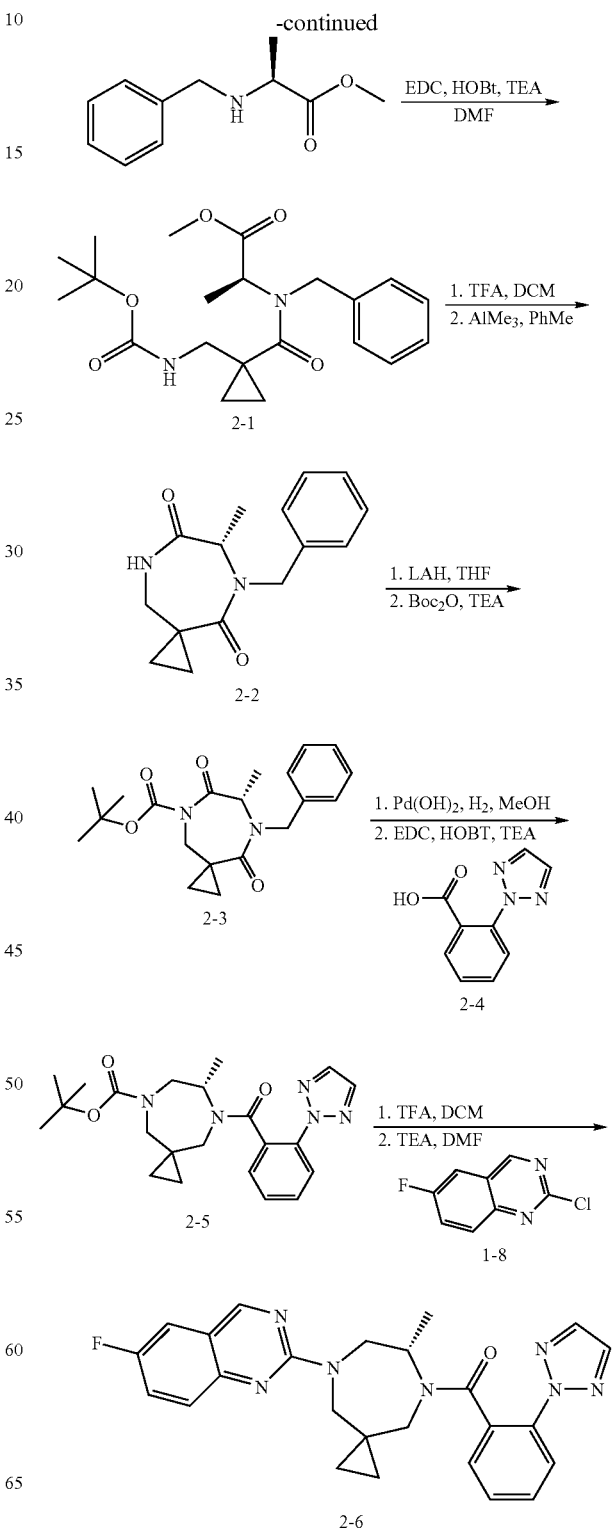

methyl N-benzyl-N-[(1-{[(tert-butoxycarbonyl)
amino]methyl}cyclopropyl)carbonyl]-L-alaninate
(2-1)

To a solution of 5.0 g Boc-APCA-OH (23.3 mmol, CHEM-IMPEX), 6.4 g (27.9 mmol) Bzl-Ala-OMe HCl, 4.65 g (30.2 mmol) 1-hydroxybenzotriazole hydrate, and 9.7 mL (70 mmol) triethylamine in 75 mL of DMF was added 5.8 g (30.2 mmol) EDC and the reaction was stirred 48 h at room temperature. The reaction was partitioned between EtOAc and 10% aqueous citric acid, the layers were separated and the organic was washed with 5% aqueous $Na_2CO_3$, then with brine, dried over $Na_2SO_4$ and concentrated by rotary evaporation. The residue was purified by column chromatography on silica gel (EtOAc/hexanes) to provide 2-1 as a white solid. Data for 3-1: LC/MS: rt=2.29 min; m/z (M+H)=391.3 found; 391.2 required.

(6S)-5-benzyl-6-methyl-5,8-diazaspiro[2.6]nonane-
4,7-dione (2-2)

A solution of 2.8 g (7.2 mmol) 2-1 in 75 mL $CH_2Cl_2$ and 5 mL TFA was allowed to stir at room temperature overnight. The solvents were removed by rotary evaporation, the residue was basified with saturated aqueous $Na_2CO_3$, and extracted with three portions of 2:1 $CHCl_3$/EtOH. The organic extracts were concentrated, redissolved in $CH_2Cl_2$, filtered and concentrated to provide a brown oil. This material was dissolved in 75 mL of toluene, cooled to 0° C. and 8.4 mL (16.9 mmol) of a 2 M solution of $AlMe_3$ in toluene was added dropwise. The reaction was allowed to slowly warm to room temperature overnight with stirring. An additional 2 mL of $AlMe_3$ was added and stirring was continued for an additional 24 h. The reaction was cooled to 0° C., carefully quenched with 100 mL of 1M HCl, and extracted with 3 portions of EtOAc. The combined organic extracts were washed with brine, dried over $Na_2SO_4$ and concentrated to provide 2-2 as a white taffy. Data for 2-2: LC/MS: rt=1.38 min; m/z (M+H)=258.1. found; 258.1 required.

tert-butyl (7S)-8-benzyl-7-methyl-5,8-diazaspiro
[2.6]nonane-5-carboxylate (2-3)

A solution of 1.35 g (5.2 mmol) 2-2 in 100 mL THF at 0° C. was treated with 6.5 mL (26.1 mmol) of a 4 M solution of LAH in THF. The reaction was slowly warmed to room temperature with stirring and allowed to stir at room temperature for 72 h. The reaction was then cooled to 0° C. and was carefully quenched with 1.2 mL water, then 1.2 mL 15% NaOH, followed by an additional 3.6 mL of water. A portion of $Na_2SO_4$ was added and the mixture was stirred for 1 h before being filtered through celite. The filtrate was concentrated to provide 1.16 g of a colorless oil. This material was dissolved in 50 mL of $CH_2Cl_2$ and 1.32 g (6 mmol) of $Boc_2O$ was added and the reaction was stirred overnight at room temperature. The reaction was concentrated and loaded directly onto a column and the residue was purified by flash column chromatography (EtOAc/hexanes) to provide 2-3 as a colorless oil. Data for 2-3: LC/MS: rt=1.43 min; m/z (M+H)=331.3. found; 331.2 required.

tert-butyl (7S)-7-methyl-8-[2-(2H-1,2,3-triazol-2-yl)
benzoyl]-5,8-diazaspiro[2.6]nonane-5-carboxylate
(2-5)

A solution of 1.26 g (3.8 mmol) 2-3 in 40 mL MeOH was evacuated under reduced pressure and purged with $N_2$ three times before adding a portion of palladium hydroxide on carbon. After purging three more times with $N_2$, the atmosphere was replaced with $H_2$ and the reaction was stirred under a balloon of $H_2$ for 2 h. The reaction was filtered through a pad of celite by rinsing with EtOAc and MeOH, and the filtrate was concentrated to provide a colorless oil. This material was dissolved in 3 mL of DMF and to it was added 683 mg of 2-4 (3.6 mmol; prepared in an analogous fashion to 1-5, see example 1-C), 668 mg (4.3 mmol) 1-hydroxybenzotriazole hydrate, 1.5 mL (10.8 mmol) triethylamine and 831 mg (4.3 mmol) EDC and the reaction was stirred overnight at 60° C. The reaction was partitioned between EtOAc and 10% aqueous citric acid, the layers were separated, and the organic was washed with water, brine, dried over $Na_2SO_4$ and concentrated by rotary evaporation. The residue was purified by column chromatography on silica gel (EtOAc/hexanes) to provide 2-5 as a white solid. Data for 2-5: LC/MS: rt=2.36 min; m/z (M+H)=412.3 found; 412.2 required.

6-fluoro-2-{(7S)-7-methyl-8-[2-(2H-1,2,3-triazol-2-
yl)benzoyl]-5,8-diazaspiro[2.6]non-5-yl}quinazoline
(2-6)

A solution of 1.03 g (2.5 mmol) 2-5 in 50 mL $CH_2Cl_2$ and 5 mL TFA was allowed to stir at room temperature overnight. The solvents were removed by rotary evaporation, the residue was basified with saturated aqueous $Na_2CO_3$, and extracted with three portions of 2:1 $CHCl_3$/EtOH. The organic extracts were concentrated, redissolved in $CH_2Cl_2$, filtered and concentrated to provide 765 mg of a taffy. A solution of 116 mg (0.37 mmol) of this material in 3 mL DMF was treated with 68 mg (0.37 mmol) of 1-8 and 130 mL (0.93 mmol) triethylamine and stirred at 60° C. overnight. After cooling to room temperature, the reaction was diluted with EtOAc, washed with saturated aqueous $NaHCO_3$, then with water, brine and dried over $Na_2SO_4$. Following concentration by rotary evaporation, the residue was purified by flash column chromatography (EtOAc/hexanes) to provide 2-6 as a pale yellow solid. Data for 2-6: HRMS (APCI) m/z (M+H) 458.2103 found; 458.2099 required.

TABLE 1

The following compounds were prepared using the foregoing methodology, but substituting the appropriately substituted reagent, as described in the foregoing Reaction Schemes and Examples. The requisite starting materials were commercially available, described in the literature or readily synthesized by one skilled in the art of organic synthesis without undue experimentation. Some final products were purified by flash chromatography ($SiO_2$; EtOAc/hexanes) and were isolated as the free-base; alternately, some products were purified by reverse phase HPLC ($CH_3CN/H_2O$ containing 0.1% TFA as a modifier) and isolated as the TFA salt, in which case the masses reported and found are for the free-base. Alternatively, fractions containing the product could be basified with $NaHCO_3$ and extracted with EtOAc, dried over $Na_2SO_4$, and concentrated to provide the free-base.

| Cmp | Structure | Name | HRMS m/z (M + H) |
| --- | --- | --- | --- |
| 1-1 | 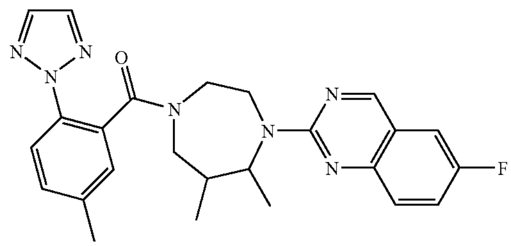 [SMILES: Cc1ccc(-n2nccn2)c(C(=O)N2CCN(c3ncc4cc(F)ccc4n3)C(C)C(C)C2)c1] | 2-{6,7-dimethyl-4-[5-methyl-2-(2H-1,2,3-triazol-2-yl)benzoyl]-1,4-diazepan-1-yl}-6-fluoroquinazoline | 460.2289 found, 460.2256 required. |
| 1-2 | 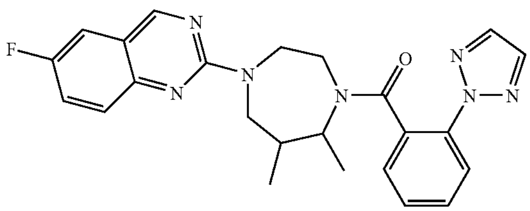 [SMILES: CC1CN(c2ncc3cc(F)ccc3n2)CCN(C(=O)c2ccccc2-n2nccn2)C1C] | 2-{5,6-dimethyl-4-[2-(2H-1,2,3-triazol-2-yl)benzoyl]-1,4-diazepan-1-yl}-6-fluoroquinazoline | 446.2122 found, 446.2099 required. |
| 1-3 | 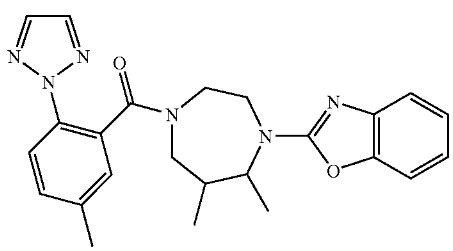 [SMILES: Cc1ccc(-n2nccn2)c(C(=O)N2CCN(c3nc4ccccc4o3)C(C)C(C)C2)c1] | 2-{6,7-dimethyl-4-[5-methyl-2-(2H-1,2,3-triazol-2-yl)benzoyl]-1,4-diazepan-1-yl}-1,3-benzoxazole | 431.221 found, 431.219 required. |
| 1-4 | 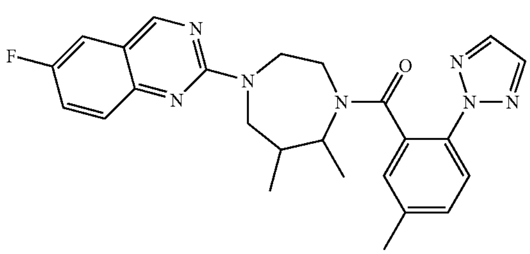 [SMILES: Cc1ccc(-n2nccn2)c(C(=O)N2CCN(c3ncc4cc(F)ccc4n3)CC(C)C2C)c1] | 2-{5,6-dimethyl-4-[5-methyl-2-(2H-1,2,3-triazol-2-yl)benzoyl]-1,4-diazepan-1-yl}-6-fluoroquinazoline | 460.2283 found, 460.2256 required. |
| 1-5 | 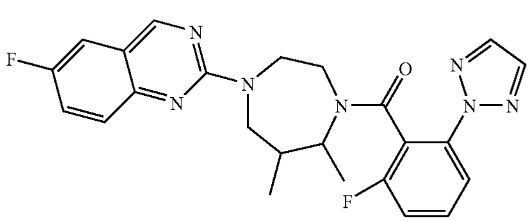 [SMILES: CC1CN(c2ncc3cc(F)ccc3n2)CCN(C(=O)c2c(F)cccc2-n2nccn2)C1C] | 6-fluoro-2-{4-[2-fluoro-6-(2H-1,2,3-triazol-2-yl)benzoyl]-5,6-dimethyl-1,4-diazepan-1-yl}quinazoline | 464.2029 found, 464.2005 required. |

TABLE 1-continued

The following compounds were prepared using the foregoing methodology, but substituting the appropriately substituted reagent, as described in the foregoing Reaction Schemes and Examples. The requisite starting materials were commercially available, described in the literature or readily synthesized by one skilled in the art of organic synthesis without undue experimentation. Some final products were purified by flash chromatography ($SiO_2$; EtOAc/hexanes) and were isolated as the free-base; alternately, some products were purified by reverse phase HPLC ($CH_3CN/H_2O$ containing 0.1% TFA as a modifier) and isolated as the TFA salt, in which case the masses reported and found are for the free-base. Alternatively, fractions containing the product could be basified with $NaHCO_3$ and extracted with EtOAc, dried over $Na_2SO_4$, and concentrated to provide the free-base.

| Cmp | Structure | Name | HRMS m/z (M + H) |
|---|---|---|---|
| 1-6 | 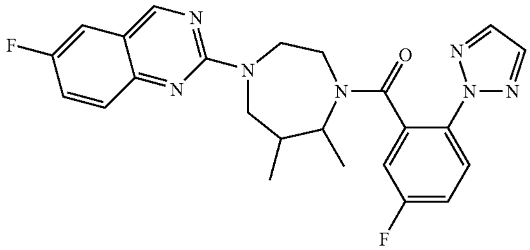 [SMILES: CC1CN(c2ncc3cc(F)ccc3n2)CCN(C(=O)c2cc(F)ccc2-n2nccn2)C1C] | 6-fluoro-2-{4-[5-fluoro-2-(2H-1,2,3-triazol-2-yl)benzoyl]-5,6-dimethyl-1,4-diazepan-1-yl}quinazoline | 464.2028 found, 464.2005 required. |
| 1-7 | 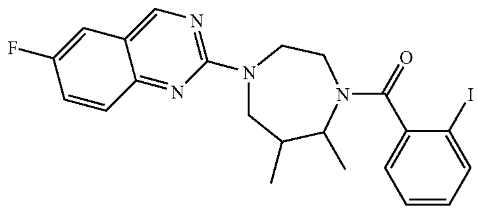 [SMILES: CC1CN(c2ncc3cc(F)ccc3n2)CCN(C(=O)c2ccccc2I)C1C] | 6-fluoro-2-[4-(2-iodobenzoyl)-5,6-dimethyl-1,4-diazepan-1-yl]quinazoline | LRMS m/z (M + H) 505.1 found, 505.34 required. |
| 1-8 | 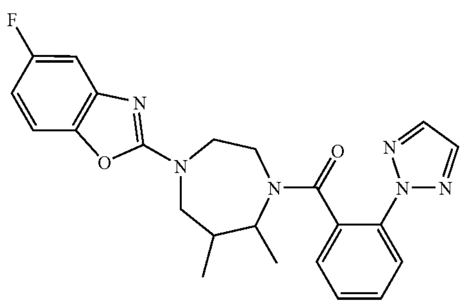 [SMILES: CC1CN(c2nc3cc(F)ccc3o2)CCN(C(=O)c2ccccc2-n2nccn2)C1C] | 2-{5,6-dimethyl-4-[2-(2H-1,2,3-triazol-2-yl)benzoyl]-1,4-diazepan-1-yl}-5-fluoro-1,3-benzoxazole | 435.1953 found, 435.194 required. |
| 1-9 | 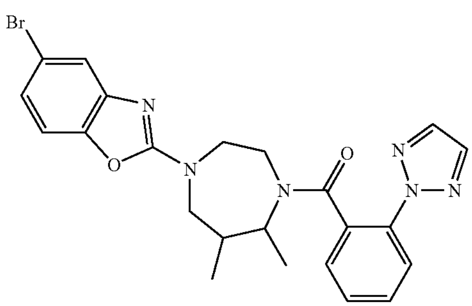 [SMILES: CC1CN(c2nc3cc(Br)ccc3o2)CCN(C(=O)c2ccccc2-n2nccn2)C1C] | 5-bromo-2-{5,6-dimethyl-4-{2-(2H-1,2,3-triazol-2-yl)benzoyl}-1,4-diazepan-1-yl}-1,3-benzoxazole | 495.1184 found, 495.1139 required. |
| 1-10 | 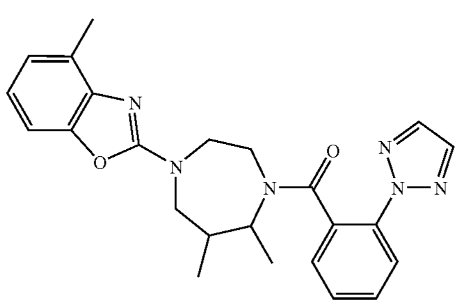 [SMILES: Cc1cccc2oc(N3CCN(C(=O)c4ccccc4-n4nccn4)C(C)C(C)C3)nc12] | 2-{5,6-dimethyl-4-{2-(2H-1,2,3-triazol-2-yl)benzoyl]-1,4-diazepan-1-yl}-4-methyl-1,3-benzoxazole | 431.2209 found, 431.219 required. |

TABLE 1-continued

The following compounds were prepared using the foregoing methodology, but substituting the appropriately substituted reagent, as described in the foregoing Reaction Schemes and Examples. The requisite starting materials were commercially available, described in the literature or readily synthesized by one skilled in the art of organic synthesis without undue experimentation. Some final products were purified by flash chromatography (SiO$_2$; EtOAc/hexanes) and were isolated as the free-base; alternately, some products were purified by reverse phase HPLC (CH$_3$CN/H$_2$O containing 0.1% TFA as a modifier) and isolated as the TFA salt, in which case the masses reported and found are for the free-base. Alternatively, fractions containing the product could be basified with NaHCO$_3$ and extracted with EtOAc, dried over Na$_2$SO$_4$, and concentrated to provide the free-base.

| Cmp | Structure | Name | HRMS m/z (M + H) |
|---|---|---|---|
| 1-11 | 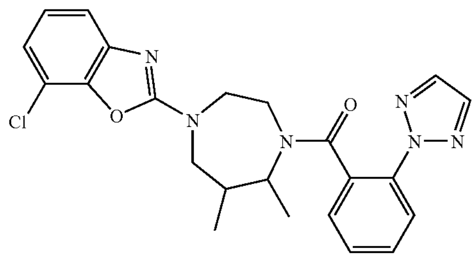 [SMILES: CC1CN(c2nc3cccc(Cl)c3o2)CCN(C(=O)c2ccccc2-n2nccn2)C1C] | 7-chloro-2-{5,6-dimethyl-4-[2-(2H-1,2,3-triazol-2-yl)benzoyl]-1,4-diazepan-1-yl}-1,3-benzoxazole | 451.1675 found, 451.1644 required. |
| 1-12 | 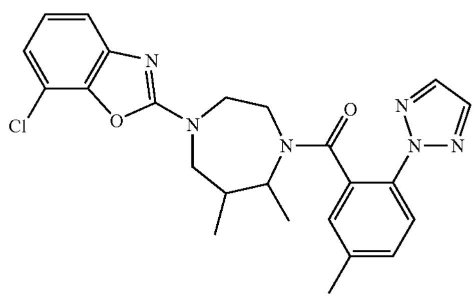 [SMILES: Cc1ccc(-n2nccn2)c(C(=O)N2CCN(c3nc4cccc(Cl)c4o3)CC(C)C2C)c1] | 7-chloro-2-{5,6-dimethyl-4-[5-methyl-2-(2H-1,2,3-triazol-2-yl)benzoyl]-1,4-diazepan-1-yl}-1,3-benzoxazole | 465.184 found, 465.1801 required. |
| 1-13 | 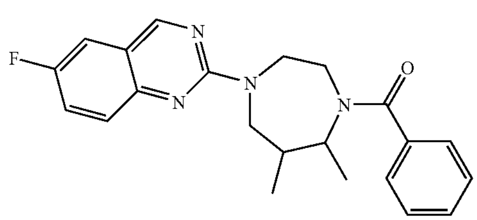 [SMILES: CC1CN(c2ncc3cc(F)ccc3n2)CCN(C(=O)c2ccccc2)C1C] | 2-(4-benzoyl-5,6-dimethyl-1,4-diazepan-1-yl)-6-fluoroquinazoline | LRMS m/z (M + H) 379.15 found, 379.44 required. |
| 1-14 | 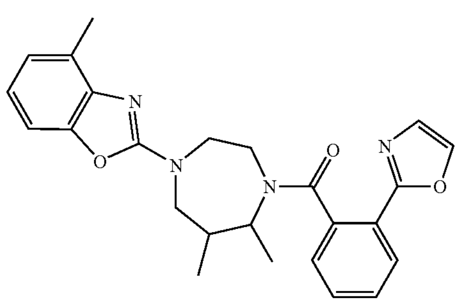 [SMILES: Cc1cccc2oc(N3CCN(C(=O)c4ccccc4-c4ncco4)C(C)C(C)C3)nc12] | 2-{5,6-dimethyl-4-[5-methyl-2-(1,3-oxazol-2-yl)benzoyl]-1,4-diazepan-1-yl}-4-methyl-1,3-benzoxazole | 445.2258 found, 445.2234 required. |

TABLE 1-continued

The following compounds were prepared using the foregoing methodology, but substituting the appropriately substituted reagent, as described in the foregoing Reaction Schemes and Examples. The requisite starting materials were commercially available, described in the literature or readily synthesized by one skilled in the art of organic synthesis without undue experimentation. Some final products were purified by flash chromatography ($SiO_2$; EtOAc/hexanes) and were isolated as the free-base; alternately, some products were purified by reverse phase HPLC ($CH_3CN/H_2O$ containing 0.1% TFA as a modifier) and isolated as the TFA salt, in which case the masses reported and found are for the free-base. Alternatively, fractions containing the product could be basified with $NaHCO_3$ and extracted with EtOAc, dried over $Na_2SO_4$, and concentrated to provide the free-base.

| Cmp | Structure | Name | HRMS m/z (M + H) |
| --- | --- | --- | --- |
| 1-15 | 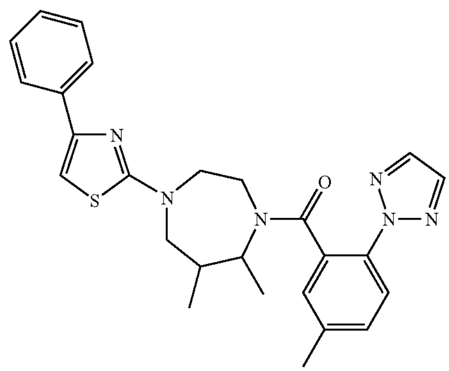 [SMILES: Cc1ccc(-n2nccn2)c(C(=O)N2CCN(c3nc(-c4ccccc4)cs3)CC(C)C2C)c1] | 5,6-dimethyl-4-[5-methyl-2-(2H-1,2,3-triazol-2-yl)benzoyl]-1-(4-phenyl-1,3-thiazol-2-yl)-1,4-diazepane | LRMS m/z (M + H) 473.47 found, 473.61 required. |
| 1-16 | 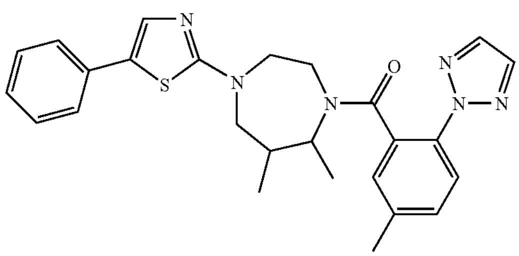 [SMILES: Cc1ccc(-n2nccn2)c(C(=O)N2CCN(c3ncc(-c4ccccc4)s3)CC(C)C2C)c1] | 5,6-dimethyl-4-[5-methyl-2-(2H-1,2,3-triazol-2-yl)benzoyl]-1-(5-phenyl-1,3-thiazol-2-yl)-1,4-diazepane | 473.2148 found, 473.2118 required. |
| 1-17 | 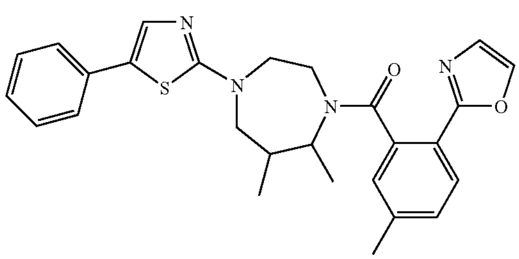 [SMILES: Cc1ccc(-c2ncco2)c(C(=O)N2CCN(c3ncc(-c4ccccc4)s3)CC(C)C2C)c1] | 5,6-dimethyl-4-[5-methyl-2-(1,3-oxazol-2-yl)benzoyl]-1-(5-phenyl-1,3-thiazol-2-yl)-1,4-diazepane | 473.2039 found, 473.2006 required. |
| 1-18 | 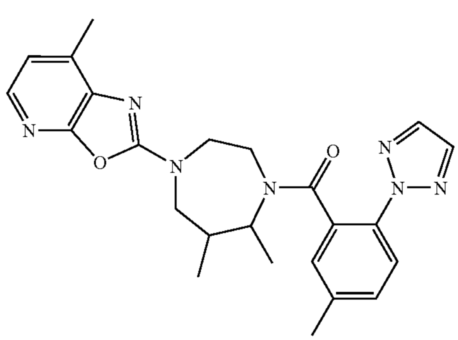 [SMILES: Cc1ccc(-n2nccn2)c(C(=O)N2CCN(c3nc4c(C)ccnc4o3)CC(C)C2C)c1] | 2-{5,6-dimethyl-4-[5-methyl-2-(2H-1,2,3-triazol-2-yl)benzoyl]-1,4-diazepan-1-yl}-7-methyl[1,3]oxazolo[5,4-b]pyridine | 446.2328 found, 446.2299 required. |

TABLE 1-continued

The following compounds were prepared using the foregoing methodology, but substituting the appropriately substituted reagent, as described in the foregoing Reaction Schemes and Examples. The requisite starting materials were commercially available, described in the literature or readily synthesized by one skilled in the art of organic synthesis without undue experimentation. Some final products were purified by flash chromatography ($SiO_2$; EtOAc/hexanes) and were isolated as the free-base; alternately, some products were purified by reverse phase HPLC ($CH_3CN/H_2O$ containing 0.1% TFA as a modifier) and isolated as the TFA salt, in which case the masses reported and found are for the free-base. Alternatively, fractions containing the product could be basified with $NaHCO_3$ and extracted with EtOAc, dried over $Na_2SO_4$, and concentrated to provide the free-base.

| Cmp | Structure | Name | HRMS m/z (M + H) |
|---|---|---|---|
| 1-19 | 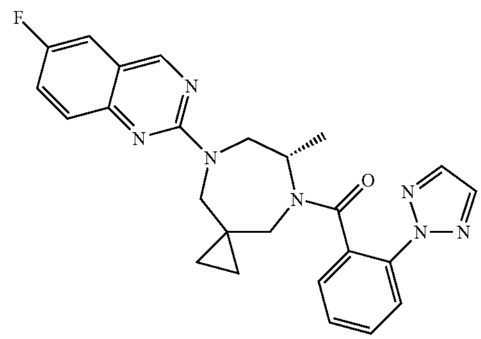 [SMILES: C[C@H]1CN(c2ncc3cc(F)ccc3n2)CC2(CC2)CN1C(=O)c1ccccc1-n1nccn1] | 6-fluoro-2-{(7S)-7-methyl-8-[2-(2H-1,2,3-triazol-2-yl)benzoyl]-5,8-diazaspiro[2.6]non-5-yl}quinazoline | 458.2103 found, 458.2099 required. |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

What is claimed is:

1. A compound of the formula Ib or Ic:

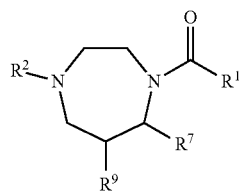

Ib

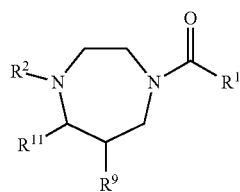

Ic wherein:
$R^1$ is selected from the group consisting of:
 (1) phenyl, where the phenyl is substituted with $R^{1a}$, $R^{1b}$ and $R^{1c}$, and
 (2) napthyl, where the napthyl is substituted with $R^{1a}$, $R^{1b}$ and $R^{1c}$;
 (3) heteroaryl, where the heteroaryl is substituted with $R^{1a}$, $R^{1b}$ and $R^{1c}$;
$R^2$ is heteroaryl, where the heteroaryl is substituted with $R^{2a}$, $R^{2b}$ and $R^{2c}$;
$R^{1a}$, $R^{1b}$, $R^{1c}$, $R^{2a}$, $R^{2b}$ and $R^{2c}$ are independently selected from the group consisting of:
 (1) hydrogen,
 (2) halogen,
 (3) hydroxyl,
 (4) —(C═O)$_m$—O$_n$—C$_{1-6}$alkyl, where m is 0 or 1, n is 0 or 1 (wherein if m is 0 or n is 0, a bond is present) and where the alkyl is unsubstituted or substituted with one or more substituents selected from $R^{13}$,
 (5) —(C═O)$_m$—O$_n$—C$_{3-6}$cycloalkyl, where the cycloalkyl is unsubstituted or substituted with one or more substituents selected from $R^{13}$,
 (6) —(C═O)$_m$—C$_{2-4}$alkenyl, where the alkenyl is unsubstituted or substituted with one or more substituents selected from $R^{13}$,
 (7) —(C═O)$_m$—C$_{2-4}$alkynyl, where the alkynyl is unsubstituted or substituted with one or more substituents selected from $R^{13}$,
 (8) —(C═O)$_m$—O$_n$-phenyl or —(C═O)$_m$—O$_n$-napthyl, where the phenyl or napthyl is unsubstituted or substituted with one or more substituents selected from $R^{13}$,
 (9) —(C═O)$_m$—O$_n$-heterocycle, where the heterocycle is unsubstituted or substituted with one or more substituents selected from $R^{13}$,
 (10) —(C═O)$_m$—NR$^{10}$R$^{11}$, wherein $R^{10}$ and $R^{11}$ are independently selected from the group consisting of:
  (a) hydrogen,
  (b) C$_{1-6}$alkyl, which is unsubstituted or substituted with one or more substituents selected from $R^{13}$,
  (c) C$_{3-6}$alkenyl, which is unsubstituted or substituted with one or more substituents selected from $R^{13}$,
  (d) cycloalkyl, which is unsubstituted or substituted with one or more substituents selected from $R^{13}$,
  (e) phenyl, which is unsubstituted or substituted with one or more substituents selected from $R^{13}$, and
  (f) heterocycle, which is unsubstituted or substituted with one or more substituents selected from $R^{13}$,
 (11) —S(O)$_2$—NR$^{10}$R$^{11}$,
 (12) —S(O)$_q$—R$^{12}$, where q is 0, 1 or 2 and where $R^{12}$ is selected from the definitions of $R^{10}$ and $R^{11}$,
 (13) —CO$_2$H,
 (14) —CN,
 (15) —NO$_2$, and
 (16) —B(OH)$_2$;

$R^7$, $R^9$, and $R^{11}$ are independently selected from the group consisting of:
(1) hydrogen,
(2) —$C_{1-6}$alkyl, where the alkyl is unsubstituted or substituted with one or more substituents selected from $R^{13}$,
(3) —O—$C_{1-6}$alkyl, where the alkyl is unsubstituted or substituted with one or more substituents selected from $R^{13}$, and
(4) -phenyl, where the phenyl is unsubstituted or substituted with one or more substituents selected from $R^{13}$, with the proviso that at least two of $R^7$, $R^9$, or $R^{11}$ are other than hydrogen;

$R^{13}$ is selected from the group consisting of:
(1) halogen,
(2) hydroxyl,
(3) —(C=O)$_m$—O$_n$—$C_{1-6}$alkyl, where the alkyl is unsubstituted or substituted with one or more substituents selected from $R^{14}$,
(4) —O$_n$—($C_{1-3}$)perfluoroalkyl,
(5) —(C=O)$_m$—O$_n$—$C_{3-6}$cycloalkyl, where the cycloalkyl is unsubstituted or substituted with one or more substituents selected from $R^{14}$,
(6) —(C=O)$_m$—$C_{2-4}$alkenyl, where the alkenyl is unsubstituted or substituted with one or more substituents selected from $R^{14}$,
(7) —(C=O)$_m$—O$_n$-phenyl or —(C=O)$_m$—O$_n$-napthyl, where the phenyl or napthyl is unsubstituted or substituted with one or more substituents selected from $R^{14}$,
(8) —(C=O)$_m$—O$_n$-heterocycle, where the heterocycle is unsubstituted or substituted with one or more substituents selected from $R^{14}$,
(9) —(C=O)$_m$—$NR^{10}R^{11}$,
(10) —S(O)$_2$—$NR^{10}R^{11}$,
(11) —S(O)$_q$—$R^{12}$,
(12) —$CO_2H$,
(13) —CN, and
(14) —$NO_2$;

$R^{14}$ is selected from the group consisting of:
(1) hydroxyl,
(2) halogen,
(3) $C_{1-6}$alkyl,
(4) —$C_{3-6}$cycloalkyl,
(5) —O—$C_{1-6}$alkyl,
(6) —O(C=O)—$C_{1-6}$alkyl,
(7) —NH—$C_{1-6}$alkyl,
(8) phenyl,
(9) heterocycle,
(10) —$CO_2H$, and
(11) —CN;

or a pharmaceutically acceptable salt thereof.

2. The compound of claim 1 wherein $R^1$ is phenyl, which is unsubstituted or substituted with one or more of:
(1) halogen,
(2) hydroxyl,
(3) —O$_n$—$C_{1-6}$alkyl, where n is 0 or 1 (wherein if n is 0, a bond is present) and where the alkyl is unsubstituted or substituted with one or more substituents selected from $R^{13}$,
(4) —O$_n$-phenyl, where the phenyl is unsubstituted or substituted with one or more substituents selected from $R^{13}$,
(5) -heterocycle, where the heterocycle is unsubstituted or substituted with one or more substituents selected from $R^{13}$,
(6) —$NR^{10}R^{11}$, wherein $R^{10}$ and $R^{11}$ are independently selected from the group consisting of:
(a) hydrogen,
(b) $C_{1-6}$alkyl, which is unsubstituted or substituted with one or more substituents selected from $R^{13}$,
(7) —S(O)$_2$—$NR^{10}R^{11}$,
(8) —$CO_2H$,
(9) —CN,
(10) —$NO_2$, and
(11) —$B(OH)_2$.

3. The compound of claim 1 wherein $R^1$ is selected from the group consisting of:
(1) phenyl,
(2) biphenyl,
(3) 2,6-dimethoxyphenyl,
(4) 2,4-dichlorophenyl,
(5) 2,6-dichlorophenyl,
(6) 2,3-difluorophenyl,
(7) 2,4-difluorophenyl,
(8) 2,6-difluorophenyl,
(9) 2-methoxy-4-methyl-phenyl,
(10) 3-methoxy-biphenyl,
(11) 3-methyl-biphenyl,
(12) 5-methyl-2-thiazolyl-phenyl, and
(13) 5-methyl-2-triazolyl-phenyl.

4. The compound of claim 1 wherein $R^2$ is heteroaryl, which is unsubstituted or substituted with one or more of:
(1) halogen,
(2) hydroxyl,
(3) —O$_n$—$C_{1-6}$alkyl, where n is 0 or 1 (wherein if n is 0, a bond is present) and where the alkyl is unsubstituted or substituted with one or more substituents selected from $R^{13}$,
(4) —O$_n$-phenyl, where the phenyl is unsubstituted or substituted with one or more substituents selected from $R^{13}$,
(5) -heterocycle, where the heterocycle is unsubstituted or substituted with one or more substituents selected from $R^{13}$,
(6) —$NR^{10}R^{11}$, wherein $R^{10}$ and $R^{11}$ are independently selected from the group consisting of:
(a) hydrogen,
(b) $C_{1-6}$alkyl, which is unsubstituted or substituted with one or more substituents selected from $R^{13}$,
(7) —S(O)$_2$—$NR^{10}R^{11}$,
(8) —$CO_2H$,
(9) —CN, and
(10) —$NO_2$.

5. The compound of claim 4 wherein $R^2$ is selected from the group consisting of:
(1) benzimidazolyl,
(2) benzothiazolyl,
(3) benzoxazolyl,
(4) quinazolinyl,
(5) quinolinyl,
(6) thiadiazolyl,
(7) thiazolyl, and
(8) oxazolopyridyl,
which is unsubstituted or substituted with halogen, hydroxyl, $C_{1-6}$alkyl, —O—$C_{1-6}$alkyl or phenyl.

6. The compound of claim 5 wherein $R^2$ is selected from the group consisting of:
(1) benzimidazol-2-yl,
(2) 1,3-benzothiazol-2-yl,
(3) 1,3-benzoxazol-2-yl,
(4) 2-quinazolinyl,
(5) 1-quinolin-2-yl, (6) 1,2,4-thiadiazol-5-yl,
(7) 1,3-thiazol-2-yl, and
(8) oxazolo[5,4-b]pyridyl,
which is unsubstituted or substituted with methyl, fluoro, chloro or phenyl.

7. The compound of claim 1 wherein $R^7$, $R^9$, and $R^{11}$ are independently selected from the group consisting of:
(1) hydrogen, and
(2) —$C_{1-6}$alkyl, where the alkyl is unsubstituted or substituted with one or more substituents selected from $R^{13}$,
with the proviso that at least two of $R^7$, $R^9$, or $R^{11}$ are other than hydrogen.

8. The compound of claim 1 wherein:
of the formula 1b wherein $R^7$ is —$C_{1-6}$alkyl and $R^9$ is —$C_{1-6}$alkyl; or
of the formula 1c wherein $R^9$ is —$C_{1-6}$alkyl and $R^{11}$ is $C_{1-6}$alkyl.

9. A compound which is selected from the group consisting
2-{6,7-dimethyl-4-[5-methyl-2-(2H-1,2,3-triazol-2-yl)benzoyl]-1,4-diazepan-1-yl}-6-fluoroquinazoline;
2-{5,6-dimethyl-4-[5-methyl-2-(2H-1,2,3-triazol-2-yl)benzoyl]-1,4-diazepan-1-yl}-6-fluoroquinazoline;
2-{6,7-dimethyl-4-[5-methyl-2-(2H-1,2,3-triazol-2-yl)benzoyl]-1,4-diazepan-1-yl}-6-fluoroquinazoline;
2-{5,6-dimethyl-4-[2-(2H-1,2,3-triazol-2-yl)benzoyl]-1,4-diazepan-1-yl}-6-fluoroquinazoline;
2-{6,7-dimethyl-4-[5-methyl-2-(2H-1,2,3-triazol-2-yl)benzoyl]-1,4-diazepan-1-yl}-1,3-benzoxazole;
2-{5,6-dimethyl-4-[5-methyl-2-(2H-1,2,3-triazol-2-yl)benzoyl]-1,4-diazepan-1-yl}-6-fluoroquinazoline;
6-fluoro-2-{4-[2-fluoro-6-(2H-1,2,3-triazol-2-yl)benzoyl]-5,6-dimethyl-1,4-diazepan-1-yl}quinazoline;
6-fluoro-2-{-4-[5-fluoro-2-(2H-1,2,3-triazol-2-yl)benzoyl]-5,6-dimethyl-1,4-diazepan-1-yl}quinazoline;
6-fluoro-2-[4-(2-iodobenzoyl)-5,6-dimethyl-1,4-diazepan-1-yl]quinazoline;
2-{5,6-dimethyl-4-[2-(2H-1,2,3-triazol-2-yl)benzoyl]-1,4-diazepan-1-yl}-5-fluoro-1,3-benzoxazole;
5-bromo-2-{5,6-dimethyl-4-[2-(2H-1,2,3-triazol-2-yl)benzoyl]-1,4-diazepan-1-yl}-1,3-benzoxazole;
2-{5,6-dimethyl-4-[2-(2H-1,2,3-triazol-2-yl)benzoyl]-1,4-diazepan-1-yl}-4-methyl-1,3-benzoxazole;
7-chloro-2-{5,6-dimethyl-4-[2-(2H-1,2,3-triazol-2-yl)benzoyl]-1,4-diazepan-1-yl}-1,3-benzoxazole;
7-chloro-2-{5,6-dimethyl-4-[5-methyl-2-(2H-1,2,3-triazol-2-yl)benzoyl]-1,4-diazepan-1-yl}-1,3-benzoxazole;
2-(4-benzoyl-5,6-dimethyl-1,4-diazepan-1-yl)-6-fluoroquinazoline;
2-{5,6-dimethyl-4-[5-methyl-2-(1,3-oxazol-2-yl)benzoyl]-1,4-diazepan-1-yl}-4-methyl-1,3-benzoxazole;
5,6-dimethyl-4-[5-methyl-2-(2H-1,2,3-triazol-2-yl)benzoyl]-1-(4-phenyl-1,3-thiazol-2-yl)-1,4-diazepane;
5,6-dimethyl-4-[5-methyl-2-(2H-1,2,3-triazol-2-yl)benzoyl]-1-(5-phenyl-1,3-thiazol-2-yl)-1,4-diazepane;
5,6-dimethyl-4-[5-methyl-2-(1,3-oxazol-2-yl)benzoyl]-1-(5-phenyl-1,3-thiazol-2-yl)-1,4-diazepane; and
2-{5,6-dimethyl-4-[5-methyl-2-(2H-1,2,3-triazol-2-yl)benzoyl]-1,4-diazepan-1-yl}-7-methyl[1,3]oxazolo[5,4-b]pyridine;
or a pharmaceutically acceptable salt thereof.

10. A pharmaceutical composition which comprises an inert carrier and a compound of claim 1 or a pharmaceutically acceptable salt thereof.

* * * * *